US010264990B2

United States Patent
Pasley et al.

(10) Patent No.: US 10,264,990 B2
(45) Date of Patent: Apr. 23, 2019

(54) METHODS OF DECODING SPEECH FROM BRAIN ACTIVITY DATA AND DEVICES FOR PRACTICING THE SAME

(71) Applicant: The Regents of the University of California, Oakland, CA (US)

(72) Inventors: Brian Pasley, Berkeley, CA (US); Robert T. Knight, El Cerrito, CA (US)

(73) Assignee: The Regents of the University of California, Oakland, CA (US)

(*) Notice: Subject to any disclaimer, the term of this patent is extended or adjusted under 35 U.S.C. 154(b) by 101 days.

(21) Appl. No.: 14/438,496

(22) PCT Filed: Oct. 25, 2013

(86) PCT No.: PCT/US2013/066967
§ 371 (c)(1),
(2) Date: Jul. 15, 2015

(87) PCT Pub. No.: WO2014/066855
PCT Pub. Date: May 1, 2014

(65) Prior Publication Data
US 2015/0297106 A1    Oct. 22, 2015

Related U.S. Application Data

(60) Provisional application No. 61/719,050, filed on Oct. 26, 2012.

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/0006* (2013.01); *A61B 5/048* (2013.01);
(Continued)

(58) Field of Classification Search
None
See application file for complete search history.

(56) References Cited

U.S. PATENT DOCUMENTS 5,447,166 A * 9/1995 Gevins ................ A61B 5/0484
128/925
5,724,987 A * 3/1998 Gevins ................ A61B 5/0484
600/544

(Continued)

FOREIGN PATENT DOCUMENTS

KR    1020080075299 A    8/2008
WO    2011127483 A1    10/2011

OTHER PUBLICATIONS

Mesgarani et al. "Influence of Context and Behavior on Stimulus Reconstruction From Neural Activity in Primary Auditory Cortex" J Neurophysiol 102: 2009, pp. 3329-3339).*

(Continued)

*Primary Examiner* — Thuykhanh Le
(74) *Attorney, Agent, or Firm* — Edward J. Baba; Khin Chin; Bozicevic, Field & Francis LLP

(57) ABSTRACT

The present disclosure provides methods of decoding speech from brain activity data. Aspects of the methods include receiving brain speech activity data from a subject, and processing the brain speech activity data to output speech feature data. Also provided are devices and systems for practicing the subject methods.

26 Claims, 22 Drawing Sheets

(51) Int. Cl.
  *A61B 5/0476* (2006.01)
  *A61B 5/0478* (2006.01)
  *A61B 5/048* (2006.01)
  *A61B 5/0484* (2006.01)
  *G10L 25/48* (2013.01)

(52) U.S. Cl.
  CPC .......... *A61B 5/0476* (2013.01); *A61B 5/0478* (2013.01); *A61B 5/04845* (2013.01); *A61B 5/4836* (2013.01); *A61B 5/6814* (2013.01); *A61B 5/6868* (2013.01); *A61B 5/6898* (2013.01); *A61B 5/741* (2013.01); *A61B 5/742* (2013.01); *G10L 25/48* (2013.01); *A61B 5/4803* (2013.01)

(56) References Cited

U.S. PATENT DOCUMENTS

| | | | | |
|---|---|---|---|---|
| 5,846,208 | A * | 12/1998 | Pichlmayr | A61B 5/048 600/544 |
| 6,011,991 | A * | 1/2000 | Mardirossian | A61B 5/0476 600/544 |
| 6,128,527 | A | 10/2000 | Howard, III et al. | |
| 2002/0059072 | A1 * | 5/2002 | Quibria | H04M 3/46 704/270 |
| 2002/0099412 | A1 | 7/2002 | Fischell et al. | |
| 2005/0043646 | A1 * | 2/2005 | Viirre | A61B 5/0482 600/545 |
| 2005/0131311 | A1 * | 6/2005 | Leuthardt | A61F 4/00 600/545 |
| 2005/0144005 | A1 * | 6/2005 | Kennedy | G10L 15/24 704/271 |
| 2005/0192805 | A1 * | 9/2005 | Kudoh | G10L 15/04 704/248 |
| 2007/0032737 | A1 * | 2/2007 | Causevic | A61B 5/048 600/544 |
| 2008/0208072 | A1 * | 8/2008 | Fadem | A61B 5/0484 600/544 |
| 2008/0287821 | A1 * | 11/2008 | Jung | G06F 19/3418 600/544 |
| 2009/0062679 | A1 * | 3/2009 | Tan | A61B 5/04012 600/544 |
| 2009/0099623 | A1 * | 4/2009 | Bentwich | A61N 1/36025 607/45 |
| 2009/0163828 | A1 * | 6/2009 | Turner | A61B 5/04845 600/559 |
| 2009/0221930 | A1 * | 9/2009 | Laken | A61B 5/0476 600/544 |
| 2009/0318825 | A1 * | 12/2009 | Kilborn | A61B 5/04842 600/544 |
| 2010/0069777 | A1 | 3/2010 | Marks | |
| 2010/0082325 | A1 * | 4/2010 | Manuel-Devadoss ("Johnson Smith") | G06F 17/28 704/2 |
| 2010/0145176 | A1 * | 6/2010 | Himes | A61B 5/0478 600/378 |
| 2011/0159467 | A1 * | 6/2011 | Peot | A61B 3/113 434/157 |
| 2011/0283190 | A1 * | 11/2011 | Poltorak | G10L 13/033 715/716 |
| 2012/0022392 | A1 * | 1/2012 | Leuthardt | A61B 5/048 600/544 |
| 2012/0101401 | A1 * | 4/2012 | Faul | A61B 5/0476 600/544 |
| 2012/0128683 | A1 * | 5/2012 | Shantha | A61K 38/08 424/141.1 |
| 2012/0158633 | A1 * | 6/2012 | Eder | G06N 5/022 706/46 |
| 2013/0018832 | A1 * | 1/2013 | Ramanathan | G06N 3/08 706/25 |
| 2013/0054240 | A1 * | 2/2013 | Jang | G06K 9/6292 704/235 |
| 2013/0096840 | A1 * | 4/2013 | Osorio | A61B 5/02055 702/19 |
| 2013/0184558 | A1 * | 7/2013 | Gallant | A61B 5/0042 600/409 |
| 2013/0261490 | A1 * | 10/2013 | Truccolo | A61B 5/0482 600/544 |
| 2013/0289658 | A1 * | 10/2013 | Denison | A61N 1/3787 607/59 |
| 2014/0081115 | A1 * | 3/2014 | Gu | A61B 5/0476 600/383 |
| 2014/0098981 | A1 * | 4/2014 | Lunner | H04R 25/70 381/320 |
| 2014/0200432 | A1 * | 7/2014 | Banerji | A61B 5/0488 600/383 |
| 2014/0211593 | A1 * | 7/2014 | Tyler | A61B 5/165 367/137 |
| 2015/0313496 | A1 * | 11/2015 | Connor | A61B 5/0476 600/301 |

OTHER PUBLICATIONS

Chi et al. "Multiresolution Spectrotemporal Analysis of Complex Sounds" Center for Auditory and Acoustics Research, Institute for System Research Electrical and Computer Engineering Department, University of Maryland, College Park, Maryland 20742, May 2005, pp. 887-906).*

* cited by examiner

METHODS OF DECODING SPEECH FROM BRAIN ACTIVITY DATA AND DEVICES FOR PRACTICING THE SAME

CROSS-REFERENCE TO RELATED APPLICATIONS

This application claims the benefit of U.S. Provisional Patent Application No. 61/719,050, filed Oct. 26, 2012; the disclosure of which is incorporated herein by reference in their entirety.

STATEMENT REGARDING FEDERALLY SPONSORED RESEARCH

This invention was made with government support under Grant No. NS021135 awarded by the National Institutes of Health. The government has certain rights in the invention.

BACKGROUND

Spoken language is a uniquely human trait. The human brain has evolved computational mechanisms that decode highly variable acoustic inputs into meaningful elements of language, such as phonemes and words. Yet for hundreds of thousands of patients, including certain patients who suffer from paralysis, locked-in syndrome, Lou Gehrig's disease, or other neurological diseases, the ability to communicate via spoken language is lacking or impaired.

SUMMARY

The present disclosure provides methods of decoding speech from brain activity data. Aspects of the methods include receiving brain speech activity data from a subject, and processing the brain speech activity data to output speech feature data. Also provided are devices and systems for practicing the subject methods.

In certain aspects, methods of the present disclosure include decoding brain speech activity of a subject into speech feature data, with such methods involving (a) receiving brain speech activity data from the subject into a decoder device; (b) processing the received brain speech activity data with a decoder module present in the decoder device, wherein the decoder module is configured to convert the received brain speech activity data into speech feature data; and (c) outputting the speech feature data to an output device.

In certain aspects, the method may also involve obtaining the brain speech activity data from the subject. The brain speech activity data may be obtained from a region of the subject's brain associated with speech recognition, with particular areas of interest including, but not limited to, the peri-sylvian language cortex including the posterior superior temporal gyrus (pSTG), motor cortex and Broca's area. The brain speech activity data itself may be the result of heard speech, imagined speech, a combination of heard and imagined speech, and/or from one or more other stimuli.

The manner in which the brain speech activity data is obtained may vary. In certain aspects, the data is obtained from a subject through the use of an electrode device which contains two or more electrodes. One or more electrodes of the device may be implanted in the subject's brain, such as by using an implanted or penetrating electrode. Where the device is implanted, the brain speech activity data may include electrocorticography (ECoG) data. Other data of interest includes, but is not necessarily limited to, electroencephalography (EEG) data and data obtained with one or more nonimplanted and/or nonpenetrating electrodes.

Brain speech activity data may be processed by variety of different algorithms or models. The processing may include a linear spectrogram model, and/or a non-linear modulation model. In certain aspects, the decoder module is configured to select between a linear spectrogram model and a non-linear modulation model.

The processed brain speech activity data may be converted by the output device. The output device may convert the speech feature data into a different form, such as into readable text or into audible sound. Such an audible sound may be, for example, a human recognizable word or collection of words (e.g., phrases or sentences).

The decoder devices that are used in practicing the subject methods may themselves vary. In certain aspects, the decoder device and the output device are integrated into a single apparatus. Where the decoder device and output device are instead part of separate apparatuses, they may be configured to share and/or transmit data (e.g., using a wired connection and/or wirelessly). Output devices of interest include, but are not limited to, computers (e.g., desktops, laptops, and tablets), phones (e.g. smartphones) and TTY devices.

Also provided by the instant disclosure are systems for practicing the subject methods. In certain aspects, the systems for decoding brain speech activity of a subject into speech feature data include a decoder device having a data input component configured to receive brain speech activity data; a decoder module having a processor and a machine-readable medium encoding instructions operable to cause the processor to convert received brain speech activity data into speech feature data and output the speech feature data to an output component; and a data output component configured to output speech feature data from the decoder module.

BRIEF DESCRIPTION OF THE DRAWINGS

The invention may be best understood from the following detailed description when read in conjunction with the accompanying drawings. Included in the drawings are the following figures.

DETAILED DESCRIPTION

Figure 1A:
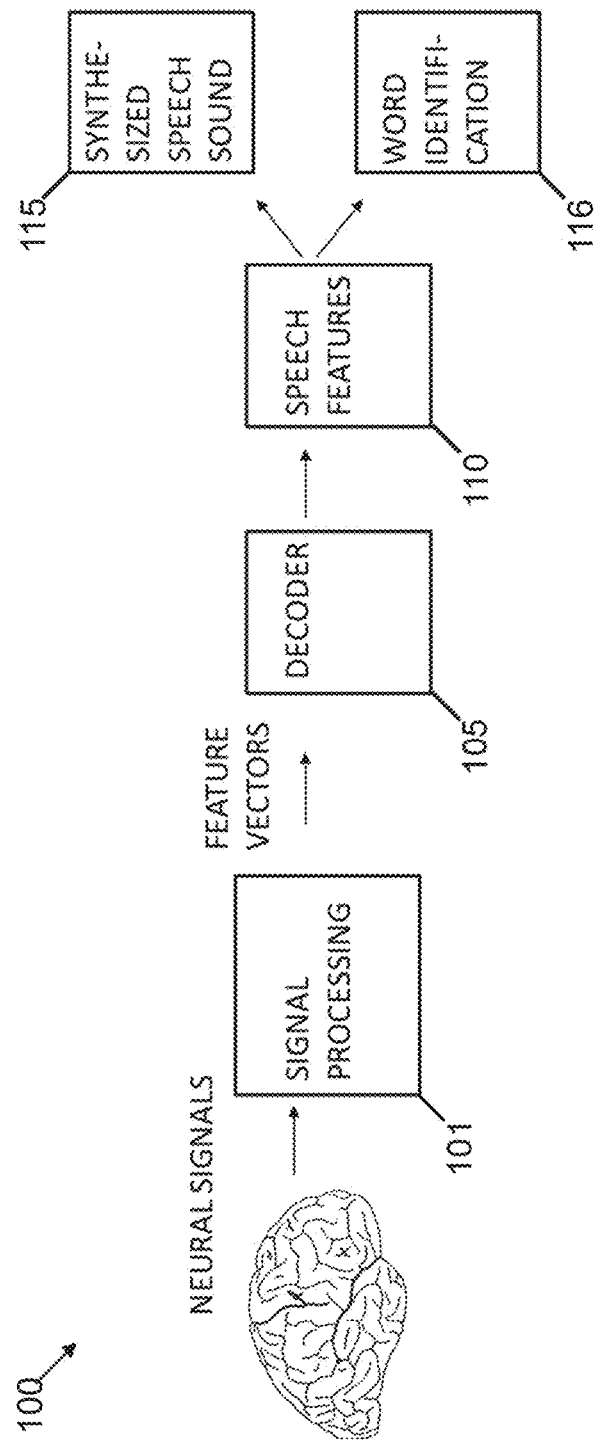
FIG. 1A depicts a flowchart of one embodiment of a method of the instant disclosure. Neural signals including brain speech activity data are received from a subject's brain. The neural signals are processed and decoded into speech features. The speech features may then be output, e.g. as synthesized speech sound or as a word identification.

The present disclosure provides methods of decoding speech from brain activity data. Aspects of the methods include receiving brain speech activity data from a subject, and processing the brain speech activity data to output speech feature data. Also provided are devices and systems for practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an electrode" includes a plurality of such electrodes and reference to "the signal" includes reference to one or more signals, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflict with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

As summarized above, aspects of the invention include methods of decoding speech from brain speech activity data. In certain aspects, the decoded brain speech activity data may be output, e.g. as speech feature data.

The phrase "brain speech activity data" is used broadly and generically to refer to any brain activity data from a subject who has heard, spoken, read, and/or imagined one or more words, pseudowords (e.g., "heef" or "thack"), phrases, and/or sentences. The phrase is meant to include, but is not limited to, raw brain activity data, such as time-varying neural signals measured as electrical activity along the scalp or as local field potentials, such as that obtained by one or more electrodes (e.g., an EEG electrode or an ECoG electrode), as shall be described more fully herein. Further, the phrase is meant to encompass brain activity data obtained from a region of the subject's brain associated with speech recognition (e.g., the peri-sylvian language cortex including the posterior superior temporal gyrus (pSTG) and Broca's area), as well as brain activity data obtained from a region of the subject's brain that is not traditionally associated with speech recognition.

Likewise, the phrase "speech feature data" is used broadly and generically to refer to brain speech activity data that has been processed. "Speech feature data" specifically includes, but is not limited to, brain speech activity data that has been processed by at least one of a linear spectrogram model and an energy model (e.g. a non-linear modulation model). Accordingly, "speech feature data" includes abstract representations (i.e., models) of speech such as spectrograms, modulation representation, phonemes, semantics, articulatory and other auditory or motor representations.

Linear spectrogram models may assume that neural responses and the spectrogram envelope are linearly related. Use of a linear spectro-temporal model in stimulus reconstruction is described in Mesgarani et al. J Neurophysiol. 2009: 102(6):3329-39; the disclosure of which in incorporated herein by reference. In contrast, energy models are non-linear and involve amplitude-based coding. Use of energy models in decoding brain activity in response to visual stimuli is described in Adelson E. H. et al. J. Opt. Soc. Am. A 2 1985: 284-299; the disclosure of which is incorporated herein by reference. In certain aspects, the energy model is a non-linear modulation model, which is based on temporal modulations and spectral modulations as is described in Chi et al. (2005) J Acoust Soc Am 118: 887-90; the disclosure of which is incorporated herein by reference.

Aspects of embodiments of methods of the present disclosure involve converting brain speech activity data into speech feature data. In certain aspects, the brain speech activity data may be received from a subject, such as by using one or more electrodes to detect the subject's brain speech activity data. In certain aspects, the brain speech activity data may be obtained from a machine-readable medium, such as a computer hard drive, memory, DVD-ROM, and the like. In such aspects, the brain speech activity data may have been previously obtained from a subject and subsequently stored in the machine-readable medium.

The brain speech activity data may be processed by a variety of different algorithms and/or models to produce speech feature data. The algorithms and/or models may together be referred to herein as a decoder module. Aspects of the methods include processing using a linear spectrogram model, a non-linear modulation model, and/or combinations of the two. The algorithms may use one or more statistical and/or machine learning algorithms, such as linear regression, principle component analysis, genetic algorithms, gradient boosting, neural networks, hidden Markov models, Bayesian networks, decision trees, and the like. In certain embodiments, the algorithms may use downsampling to reduce computational load. The algorithms may minimize overfitting (e.g., through cross validation, by limiting the number of learning iterations, etc.). For a general review of statistical methods and machine learning, see Larrañaga P. et al. Machine learning in bioinformatics. Brief Bioinform. 2006: 7(1):86-112; the disclosure of which is incorporated by reference. Once processed, speech feature data may be output, such as by an output device.

FIG. 1A presents a flow diagram of a method 100 of the instant disclosure, intended to be a general and non-limiting illustration. Neural signals from a subject's brain are processed 101 using a decoder 105, resulting in speech feature data 110. The decoder 105 may include a data input component configured to receive brain speech activity data; a decoder module comprising a processor that is configured to convert received brain speech activity data into speech feature data; and a data output component configured to output speech feature data from the decoder module. The processing 101 may involve, for example, the use of a linear spectrogram model, a non-linear modulation model, and/or combinations of the two. The speech feature data 110 may be output, such as in the form of synthesized speech sound 115 and/or as readable text 116.

Figure 1B:
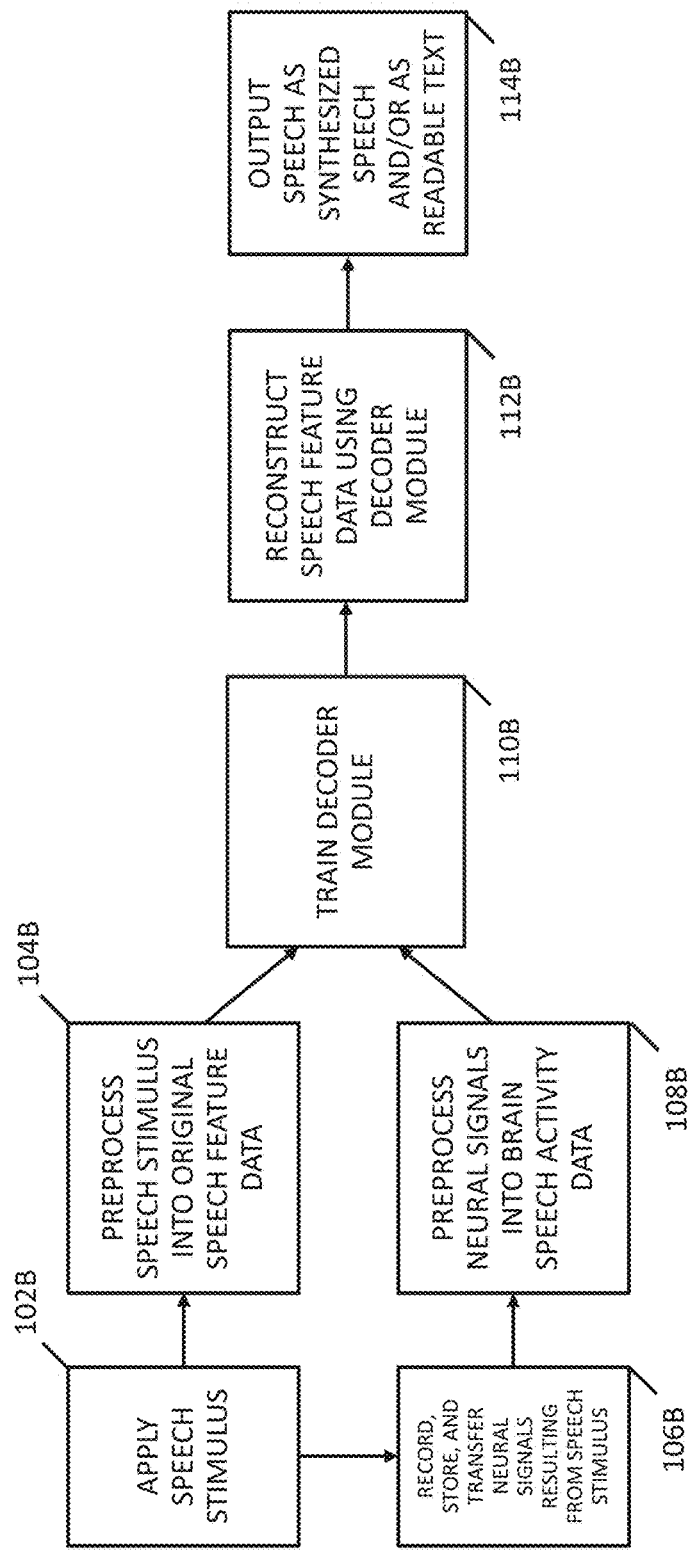
FIG. 1B depicts a flowchart of one embodiment of a method of the instant disclosure, in which a decoder module is trained. A speech stimulus is applied to a subject (e.g. a subject listens to speech sounds, speaks out loud, or imagines speech sounds, movement, and/or other speech representations). The speech stimulus is preprocessed into original speech feature data (to be used as output data for the decoding module). The neural signals resulting from the speech stimulus are preprocessed into brain speech activity data (e.g. neural input features). The original speech feature data and the brain speech activity data are used to train (e.g. build, test, etc.) the decoding module (e.g. a predictive decoding model). The decoding module generates reconstructed speech feature data (i.e. predicted speech feature data), from the brain speech activity data, which is output as speech (e.g. by an output device). The output speech may be in the form of synthesized speech and/or readable text.

FIG. 1B presents a flowchart of one embodiment of a method of the instant disclosure, in which a decoder module (e.g. of the decoder 105 of FIG. 1A) is trained. A speech stimulus is applied 102B to a subject (e.g. a subject listens to speech sounds, speaks outloud, or imagines speech sounds, movement, and/or other speech representations).

The speech stimulus is preprocessed 104B into original speech feature data (e.g. as an auditory spectrogram, auditory modulation data, phonetics, semantics, articulatory motor data, and/or other stimulus representations of speech comprehension and production). The neural signals resulting from the speech stimulus are recorded, stored, and transferred 106B. The neural signals are preprocessed 108B into brain speech activity data (e.g. neural input features). Steps 106B and 108B may occur independently of (e.g. before, after, or at the same time as) step 104B. The decoding module (i.e. a predictive decoding model) may be trained 110B based on the brain speech activity data and/or the original speech feature data.

In certain embodiments, the training of the decoder module may involve use of the algorithms, models, statistical methods, and/or machine learning algorithms as previously discussed. The training of the decoder module may involve fitting one or more models (e.g. linear model, non-linear modulation model) to a training set (e.g. comprising the applied stimulus, brain speech activity data and/or reconstructed speech feature data). The decoder module may reconstruct 112B speech feature data from the brain speech activity data. An output device (e.g. part of or external to the decoder 105) may output 114B reconstructed speech feature data as speech (e.g. synthesized speech and/or as readable text). In certain aspects, this method may be performed iteratively. The training 110B of the decoder module may be based on a number of speech stimuli and resulting brain speech activity data and/or original speech feature data. In certain embodiments, the output device may apply one or more statistical methods and/or machine learning algorithms (such as those described for the decoding module) to classify, or otherwise identify, the speech feature data (or sections thereof) as one or more phonemes, words, pseudowords, phrases, commands, actions, and/or sentences. In certain embodiments, the output device may use highest probability and/or a model score to classify the speech feature data.

Figure 1C:
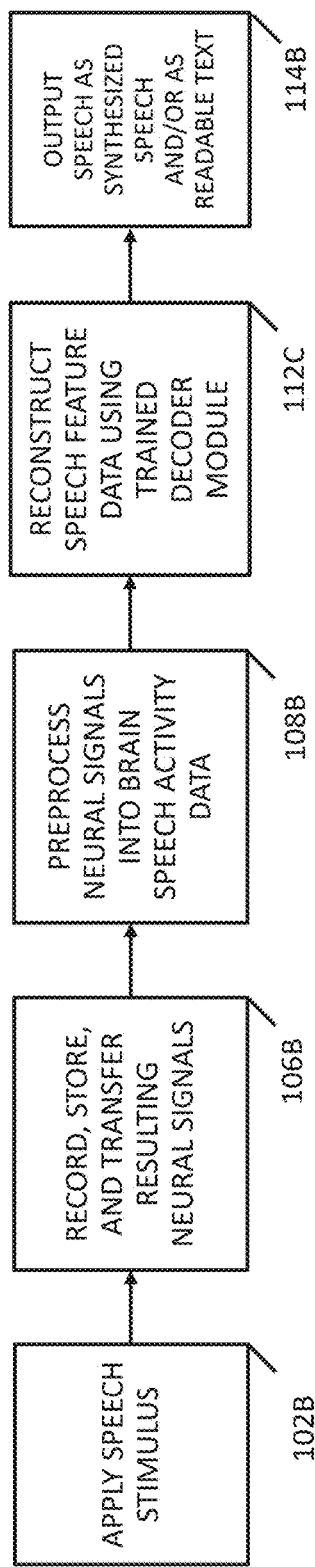
FIG. 1C depicts a flowchart of one embodiment of a method of the instant disclosure, which uses the trained decoder module of FIG. 1B. Steps for preprocessing speech stimulus into original speech feature data and training the decoder module are not necessary in this embodiment.

FIG. 1C presents a flowchart of one embodiment of a method of the instant disclosure, which uses the trained decoder module of FIG. 1B to reconstruct 112C speech feature data. Steps for preprocessing speech stimulus into original speech feature data and training the decoder module may not be necessary in this embodiment. Various steps and aspects of the methods shall now be described in greater detail below.

Receiving Brain Speech Activity Data

Aspects of embodiments of the invention include receiving brain speech activity data for a subject. Brain speech activity data may be the result of heard speech, imagined speech, a combination of heard and imagined speech, and/or from one or more other stimuli.

The term "heard speech" is used to refer to one or more words, pseudowords (e.g., "heef" or "thack"), phrases, and/or sentences that are heard by a subject. Heard speech may include sounds made by the subject, or that the subject hears from one or more other individuals. In contrast, "imagined speech" is used to refer to one or more words, pseudowords, phrases, and/or sentences that are thought and/or inaudibly spoken by a subject.

In certain aspects, the brain speech activity data may be obtained from a machine-readable medium, such as a computer hard drive, memory, DVD-ROM, and the like. In such aspects, the brain speech activity data may have been previously obtained from a subject and subsequently stored in the machine-readable medium. Such brain speech activity data may have been stored non-transiently, such as for about 1 ms or more, including about 10 ms or more, about 100 ms or more, e.g. about 1 s or more, about 10 s or more, about 30 s or more, about 60 s or more, about an hour or more, or about a day or more.

In certain aspects, receiving brain speech activity for a subject may involve receiving brain speech activity data from the subject, such as by using one or more electrodes. Methods of the present disclosure thus may include methods of decoding speech from brain speech activity data received from a patient substantially in real time, including methods in which time between obtaining the brain speech activity data from the subject and outputting the speech feature data to an output device is about 30 seconds or less, e.g., 10 seconds or less, or 5 seconds or less, including 1 second or less.

Figure 2:
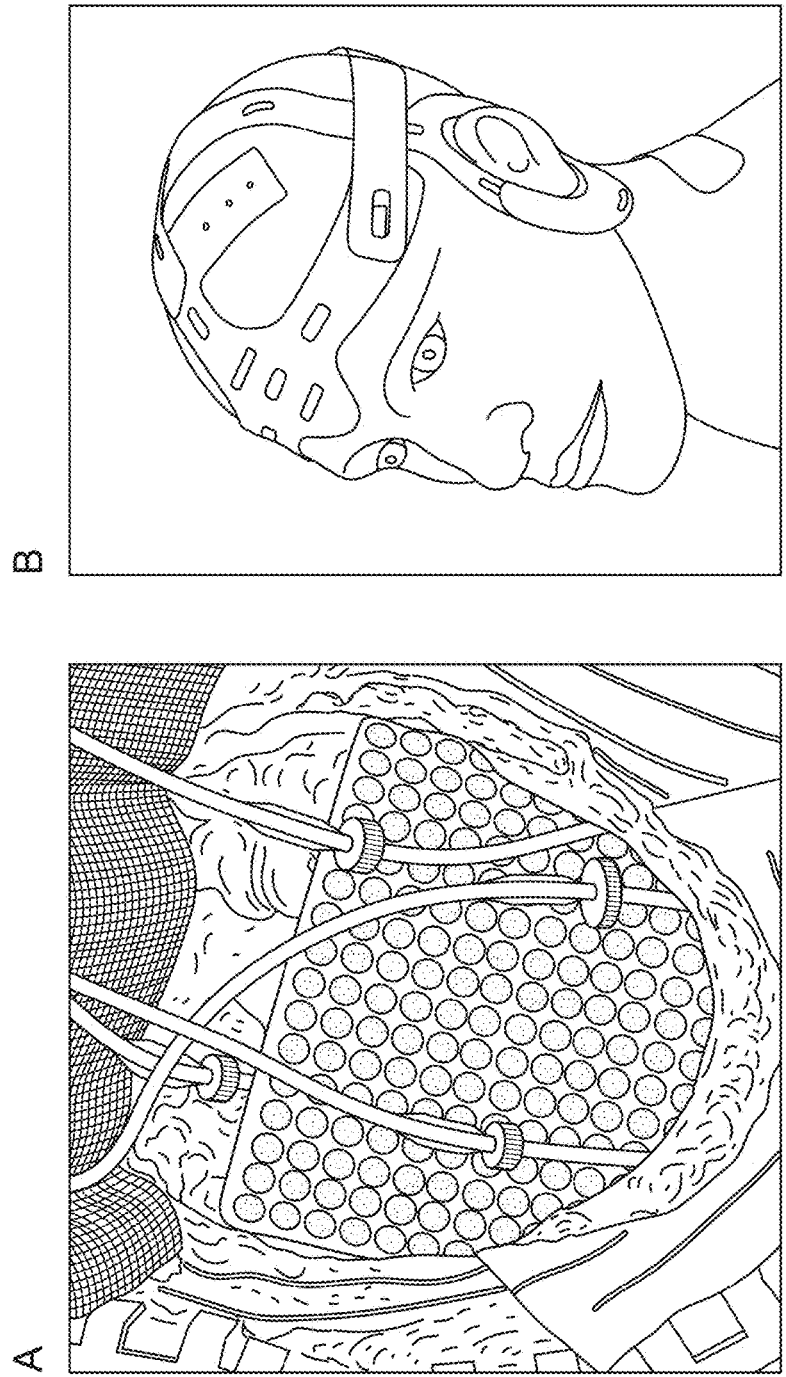
FIG. 2, Panels A-B illustrate non-limiting examples of electrodes for use in recording speech-related brain signals. Panel A: Implanted electrode array for direct recording of speech-related brain signals. Panel B: Noninvasive scalp electrode system.

Brain speech activity data may be detected and/or collected from a subject by any convenient means. In certain instances, receiving a subject's brain speech activity data includes positioning one or more electrodes, wherein the electrode(s) are of a suitable type and position so as to detect a subject's brain activity. FIG. 2, Panels A-B illustrate two of the many possible ways in which electrodes may be positioned in accordance with the instant disclosure. In the embodiment illustrated in FIG. 2, Panel A, an electrode array is implanted in the subject's brain for detecting brain speech activity data, where each numbered white circle corresponds to a separate electrode. FIG. 2, Panel B shows an embodiment in which a plurality of noninvasive electrodes are placed over a subject's head to record brain speech activity data, such as EEG data.

In certain aspects, one or more electrodes may be positioned so as to correspond to particular landmarks or regions in the subject's brain. The specific location at which to position an electrode may be determined by identification of anatomical landmarks in a subject's brain, such as the pre-central and post-central gyri and the central sulcus. Identification of anatomical landmarks in a subject's brain may be accomplished by any convenient means, such as magnetic resonance imaging (MRI), functional magnetic resonance imaging (fMRI), positron emission tomography (PET), and visual inspection of a subject's brain while undergoing a craniotomy. Once a suitable location for an electrode is determined, the electrode may be positioned or implanted according to any convenient means. Suitable locations for positioning or implanting an electrode may include, but are not limited to, one or more regions of the subject's brain associated with speech recognition, including the peri-sylvian language cortex including the posterior superior temporal gyrus (pSTG) and Broca's area. In certain aspects, correct placement of electrodes may be confirmed by any convenient means, including visual inspection or computed tomography (CT) scan. In some aspects, after electrode positions are confirmed they may be superimposed on a surface reconstruction image of the subject's brain.

Methods of interest for positioning electrodes further include, but are not limited to, those described in U.S. Pat. Nos. 4,084,583; 5,119,816; 5,291,888; 5,361,773; 5,479,934; 5,724,984; 5,817,029; 6,256,531; 6,381,481; 6,510,340; 7,239,910; 7,715,607; 7,908,009; 8,045,775; and 8,019,142; the disclosures of which are incorporated herein by reference.

Though in some embodiments one electrode may positioned, in some embodiments more than one electrode may be positioned. More than one electrode may be employed so as to provide greater resolution or information about the brain speech activity data, as each electrode may convey information about the activity of a particular region. By comparing differences between the signals of each electrode, more accurate models of brain speech activity data may be created (FIG. 6, Panel C; Example 1). Accordingly, in certain embodiments, between about 5 and 1024 electrodes, or more, may be employed. In some embodiments, the number of electrodes positioned is about 5 to 10 electrodes, about 10 to 20 electrodes, about 20 to 30 electrodes, about 30 to 40 electrodes, about 40 to 50 electrodes, about 60 to 70 electrodes, about 70 to 80 electrodes, about 80 to 90 electrodes, about 90 to 100 electrodes, about 100 to 110 electrodes, about 110 to 120 electrodes, about 120 to 130 electrodes, about 130 to 140 electrodes, about 140 to 150 electrodes, about 150 to 160 electrodes, about 160 to 170 electrodes, about 170 to 180 electrodes, about 180 to 190 electrodes, about 190 to 200 electrodes, about 200 to 210 electrodes, about 210 to 220 electrodes, about 220 to 230 electrodes, about 230 to 240 electrodes, about 240 to 250 electrodes, about 250 to 300 electrodes, about 300 to 400 electrodes, about 400 to 500 electrodes, about 500 to 600 electrodes, about 600 to 700 electrodes, about 700 to 800 electrodes, about 800 to 900 electrodes, about 900 to 1000 electrodes, or about 1000 to 1024 electrodes, or more. When more than one electrode is employed, the electrodes may be homogeneous or heterogeneous.

Figure 3:
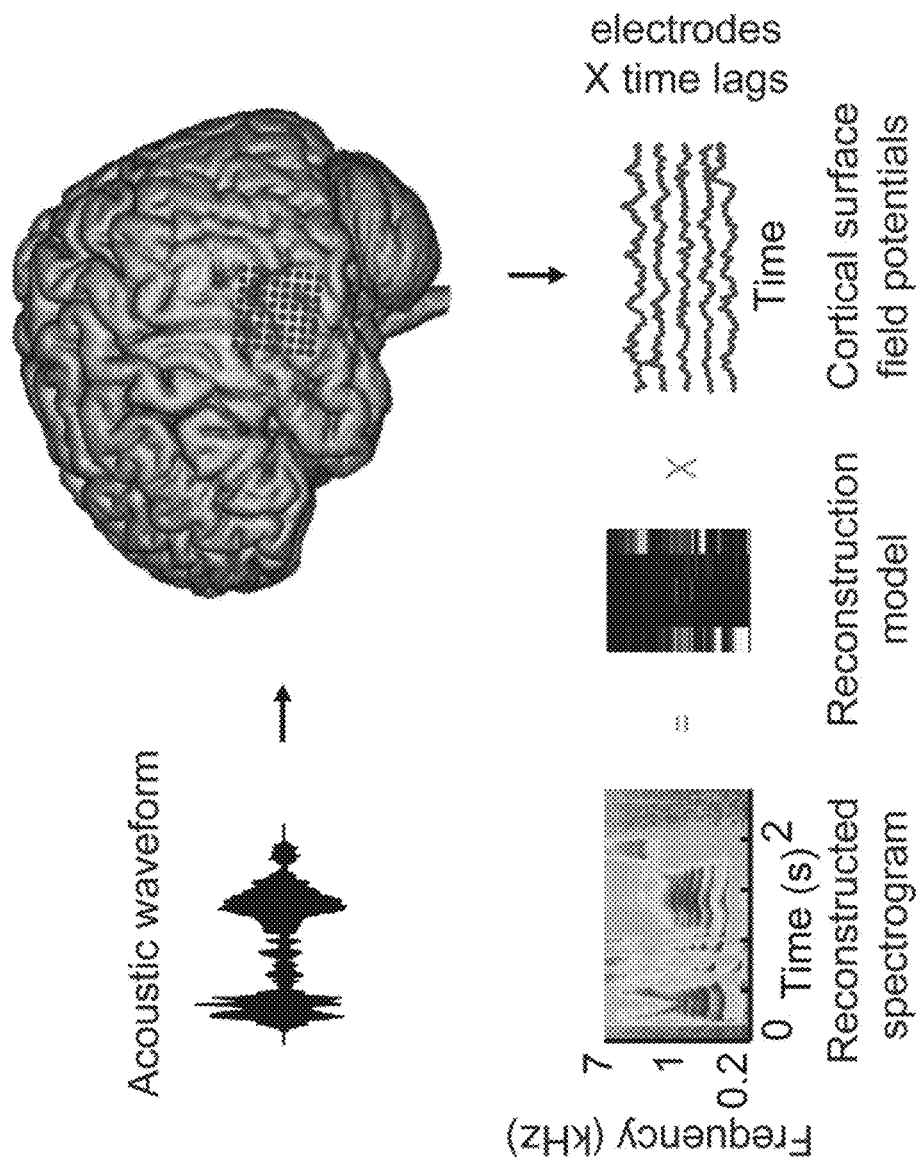
FIG. 3 depicts an overview of certain aspects an experimental paradigm. Participants listened to words (acoustic waveform, top left), while neural signals were recorded from cortical surface electrode arrays (top right, solid gray circles) implanted over superior and middle temporal gyrus (STG, MTG). Speech-induced cortical field potentials (bottom right, gray curves) recorded at multiple electrode sites were used to fit multi-input, multi-output models for offline decoding. The models take as input time-varying neural signals at multiple electrodes and output a spectrogram consisting of time-varying spectral power across a range of acoustic frequencies (180-7,000 Hz, bottom left). To assess decoding accuracy, the reconstructed spectrogram is compared to the spectrogram of the original acoustic waveform. Where a speech feature data representation other than a spectrogram is utilized, decoding accuracy may be assessed by comparing to the reconstructed speech features to the original speech features.
Figure 11:
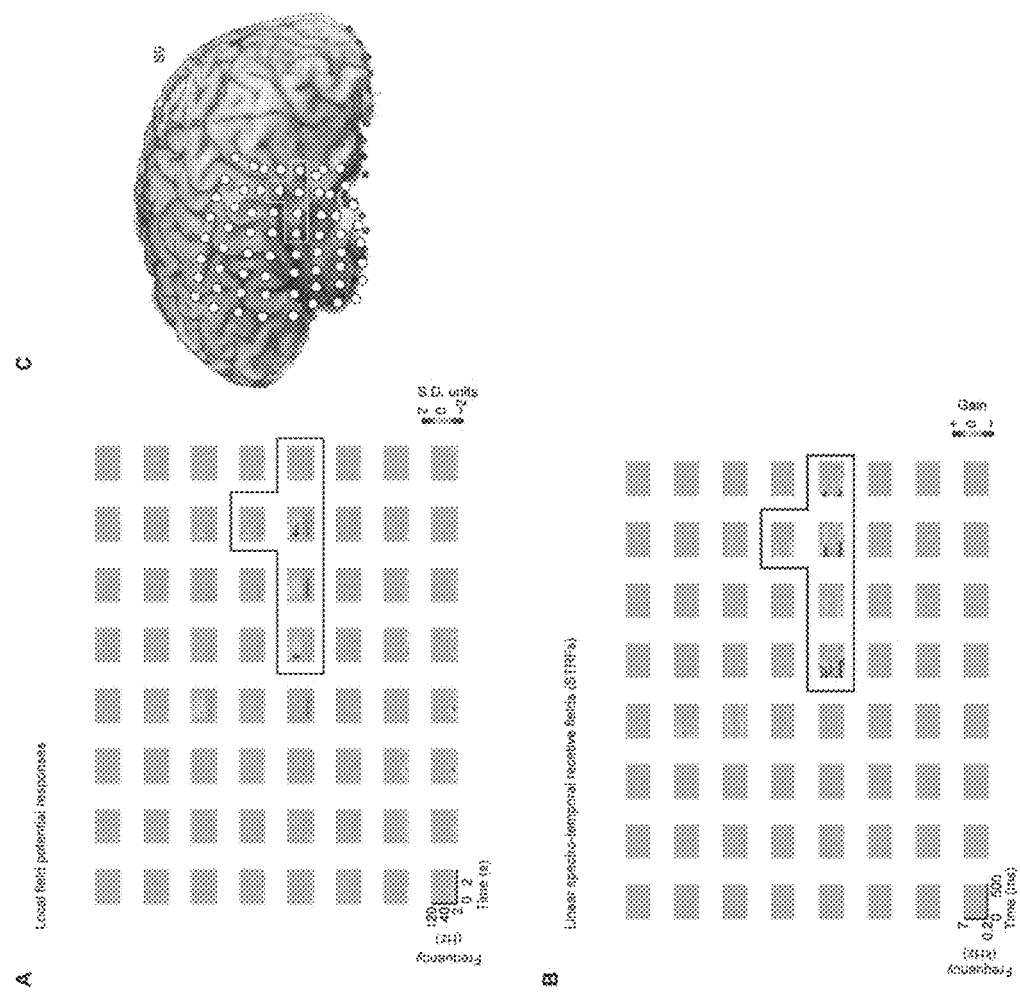
FIG. 11, Panels A-C show anatomical distribution of surface local field potential (LFP) responses and linear STRFs in a low density grid participant (10 mm electrode spacing). Panel A: Trial averaged spectral LFP responses to English sentences (2-4 s duration) at individual electrode sites. Speech stimuli evoke increased high gamma power (~70-150 Hz) sometimes accompanied by decreased power at lower frequencies (<40 Hz) throughout sites in the temporal auditory cortex. Black outline indicates temporal cortex sites with high gamma responses (>0.5 SD from baseline). Panel B: Example linear STRFs across all sites for one participant. All models are fit to power in the high gamma band range (70-150 Hz). Panel C: Anatomical location of subdural electrode grid (10 mm electrode spacing). Black box outline indicates sites as in Panels A and B.

As is apparent from FIGS. 2, 3, 11, Panel C and 18, Panel C, electrodes may be arranged in no particular pattern or any convenient pattern to facilitate recording of brain speech activity data. For example, a plurality of electrodes may be placed in a grid pattern, in which the spacing between adjacent electrodes is approximately equivalent. Such spacing between adjacent electrodes may be, for example, about 2.5 cm or less, about 2 cm or less, about 1.5 cm or less, about 1 cm or less, about 0.5 cm or less, about 0.1 cm or less, or about 0.05 cm or less. Electrodes placed in a grid pattern may be arranged such that the overall plurality of electrodes forms a roughly geometrical shape. In certain embodiments, a grid pattern may be roughly square in overall shape, roughly rectangular, or roughly trapezoidal.

Electrodes may also be pre-arranged into an array, such that the array includes a plurality of electrodes that may be placed on or in a subject's brain. Such arrays may be miniature- or micro-arrays, a non-limiting example of which may be a miniature ECoG array. An array may include, for example, about 5 electrodes or more, e.g., about 5 to 10 electrodes, about 10 to 20 electrodes, about 20 to 30 electrodes, about 30 to 40 electrodes, about 40 to 50 electrodes, about 50 to 60 electrodes, about 60 to 70 electrodes, about 70 to 80 electrodes, about 80 to 90 electrodes, about 90 to 100 electrodes, about 100 to 125 electrodes, about 125 to 150 electrodes, about 150 to 200 electrodes, about 200 to 250 electrodes, about 250 to 300 electrodes, about 300 to 400 electrodes, about 400 to 500 electrodes, or about 500 electrodes or more. In certain embodiments, the array may cover a surface area of about 1 cm$^2$, about 1 to 10 cm$^2$, about 10 to 25 cm$^2$, about 25 to 50 cm$^2$, about 50 to 75 cm$^2$, about 75 to 100 cm$^2$, or 100 cm$^2$ or more. Arrays of interest may include, but are not limited to, those described in U.S. Pat. Nos. U.S. D565,735; U.S. D603,051; U.S. D641,886; and U.S. D647,208; the disclosures of which are incorporated herein by reference.

Electrodes may be platinum-iridium electrodes or be made out of any convenient material. The diameter, length, and composition of the electrodes to be employed may be determined in accordance with routine procedures known to those skilled in the art. Factors which may be weighted when selecting an appropriate electrode type may include but not be limited to the desired location for placement, the type of subject, the age of the subject, cost, duration for which the electrode may need to be positioned, and other factors.

In certain embodiments, the electrodes may be intracranial electrodes. Such electrodes may be implanted between a subject's scalp and a subject's skull. Intracranial electrodes may be positioned and arranged as described previously.

In some embodiments, the electrodes may be ECoG electrodes or may include an ECoG array. The ECoG electrodes may be intracranial, and may be implanted between a subject's scalp and a subject's skull or directly on the surface of the brain. For a general review of ECoG technology, see Ajmone-Marsan, C. Electrocorticography: Historical Comments on its Development and the Evolution of its Practical Applications, *Electroencephalogr. Clin. Neurophysiol, Suppl.* 1998, 48: 10-16; the disclosure of which is incorporated herein by reference.

Also of interest are electrodes that may receive electroencephalography (EEG) data. One or more wet or dry EEG electrodes may be used in practicing the subject methods. Electrodes and electrode systems of interest further include, but are not limited to, those described in U.S. Patent Publication Numbers 2007/0093706, 2009/0281408, 2010/0130844, 2010/0198042, 2011/0046502, 2011/0046503, 2011/0046504, 2011/0237923, 2011/0282231, 2011/0282232 and U.S. Pat. Nos. 4,709,702, 4,967,038, 5,038,782, 6,154,669; the disclosures of which are incorporated herein by reference.

In certain embodiments, a ground electrode or reference electrode may be positioned. A ground or reference electrode may be placed at any convenient location, where such locations are known to those of skill in the art. In certain embodiments, a ground electrode or reference electrode is a scalp electrode. A scalp electrode may be placed on a subject's forehead or in any other convenient location.

Processing

The brain speech activity data may be processed to produce speech feature data. Such processing may be carried out by a decoder device. As used herein, "decoder device" is intended to be used broadly and generically to refer to an apparatus that is configured to convert brain speech activity data to speech feature data. The phrase "decoder device" may include, but is not limited to, computers (e.g. laptop, desktop, server, cloud server, etc.), neurophysiology workstations (e.g. a RZ2 Neurophysiology Workstation sold by Tucker Davis Technologies), smartphones/tablets, and the like. In certain aspects, a decoder device includes a data input component to receive brain speech activity data, a decoder module that converts received brain speech activity data into speech feature data, and a data output component configured to output speech feature data from the decoder module.

Decoder devices of interest may include a data input component that may receive brain speech activity data. In certain aspects, the data input component may include any convenient means for obtaining brain speech activity data for a subject that is contained in a non-transient storage medium, such as RAM memory, flash memory, hard disk, etc.

In certain aspects, the data input component is configured to receive brain speech activity data from a subject via direct physical communication, such as a by a cable. For example, an electrode may be placed on a subject, wherein the electrode is connected to a wire that is in physical connection with the data input component of a decoder device. A data input component may thus be configured to physically connect with a plurality of electrodes, such as 2 or more, including 10 or more, e.g., 50 or more, or 100 or more.

A data input component may also, or instead, receive brain speech activity data by a non-physical means. Of interest is wireless communication, such as Wi-Fi, cellular (e.g., 3G, 4G), Bluetooth and the like; a non-limiting example of such wireless communication is described in US Patent Publication 2006/0129056; the disclosure of which is incorporated herein by reference.

Decoder devices may include a decoder module that converts received brain speech activity data into speech feature data. The decoder module may contain at least one processor that is configured to convert brain speech activity data to speech feature data. In certain aspects, the processor may execute instructions from one or more software modules to convert brain speech activity data to speech feature data, and/or to output the speech feature data to an output component. A software module may reside in RAM memory, flash memory, ROM memory, EPROM memory, EEPROM memory, registers, hard disk, a removable disk, a CD-ROM, or any other form of storage medium known in the art. A storage medium may be coupled to the processor such that the processor can read information from, and write information to, the storage medium. In the alternative, the storage medium may be integral to the processor.

The brain speech activity data received by the decoder module may contain brain activity data covering a wide range of frequencies. The frequencies contained within the brain speech activity data may depend upon factors including but not limited to the particular type of electrode employed, the type of subject, the position of the electrode, and other factors. In certain embodiments, the brain speech activity data received by a decoder module may include frequencies of about 1 Hz to 500 Hz or more. In certain embodiments, the brain speech activity data may include frequencies from the range of about 1 to 10 Hz, about 10 to 20 Hz, about 20 to 30 Hz, about 30 to 40 Hz, about 40 to 50 Hz, about 50 to 60 Hz, about 60 to 70 Hz, about 70 to 80 Hz, about 80 to 90 Hz, about 90 to 100 Hz, about 100 to 125 Hz, about 125 Hz to 150 Hz, about 150 Hz to 175 Hz, about 175 Hz to 200 Hz, about 200 Hz to 225 Hz, about 225 Hz to 250 Hz, about 250 Hz to 275 Hz, about 275 Hz to 300 Hz, about 300 Hz to 325 Hz, about 325 Hz to 350 Hz, about 350 Hz to 375 Hz, about 375 Hz to 400 Hz, about 400 Hz to 425 Hz, about 425 Hz to 450 Hz, about 450 Hz to 475 Hz, or about 475 Hz to 500 Hz or more. In some embodiments, the brain speech activity data received by the decoder module may include delta, theta, alpha, mu, beta, gamma, or high gamma frequencies. Certain embodiments may include only one of delta, theta, alpha, mu, beta, gamma, and high gamma frequency bands. Other embodiments may include one or more of delta, theta, alpha, mu, beta, gamma, and high gamma frequency bands.

In certain aspects, the decoder module may process the received brain speech activity data prior to converting the data into speech feature data. Processing may include applying one or more filters, such as a bandpass filter, a notch filter, a temporal filter, and/or a spectro-temporal filter. Processing may include applying a transform to the brain speech activity data.

For example, in certain aspects processing may include applying a bandpass filter to the brain speech activity data. A bandpass filter may separate the brain speech activity data in about 2 to about 16 different frequency bands, or more. In certain embodiments, a bandpass filter may split a signal into about 2 frequency bands, about 4 frequency bands, about 6 frequency bands, about 8 frequency bands, about 10 frequency bands, about 12 frequency bands, about 14 frequency bands, about 16 frequency bands or more. Specific frequency bands may be selected to divide brain speech activity data into physiologically important ranges. In some embodiments, a bandpass filter is employed to produce a signal including mu frequencies, beta frequencies, gamma frequencies, high gamma frequencies, or other ranges known to correspond to particular brain wave frequencies.

The decoder module may apply one or more notch filters to the brain speech activity data. A notch filter may be applied any frequency for which signal subtraction is desired. In certain embodiments, a notch filter may be used that filters frequencies at about 60 Hz, at about 120 Hz, or about 180 Hz. A notch filter may be applied to remove electrical hum or other noise, such as that from an A/C current.

A decoder module may transform brain speech activity data. For example, high gamma band power (about 70-150 Hz) brain speech activity data may be extracted from an input signal by any convenient means, such as applying a Hilbert-Huang transform. The decoder module may apply other transformations and/or filters to the brain speech activity data (e.g. to remove artifacts, reduce background, and/or extract brain speech activity data) as described by Sanai et al. (2007) EEG Signal Processing, the disclosure of which is incorporated by reference. Processing may also involve converting an input signal into standardized z-scores, using any convenient means.

The processed or unprocessed brain speech activity data may be converted by the decoder module into speech feature data. In certain aspects, conversion of brain speech activity data into speech feature data may involve application of a linear spectrogram model and/or a non-linear modulation model. The linear spectrogram model and/or the non-linear modulation model may be contained in one or more software modules that reside in a storage medium that is coupled to the processor of the decoder module, as described above.

In certain aspects, the decoder module may select between a linear spectrogram model and a non-linear modulation model for converting brain speech activity data to speech feature data. The decoder module may apply a linear spectrogram model to a subset of brain speech activity data, and a non-linear modulation model to a subset of the brain speech activity data. In such aspects, the decoder module may include instructions as to when to apply a linear spectrogram model and when to apply a non-linear modulation model.

Alternatively, the decoder module may apply both a linear spectrogram model and a non-linear modulation model to convert the brain speech activity data to speech feature data. The resulting speech feature data from each model may be combined and/or averaged by any convenient means. In certain aspects, the linear spectrogram model and non-linear modulation model may be applied with equal or unequal weights by the decoder module. The weights that may be applied to each individual model may vary, e.g., according to the frequency of the brain speech activity data.

The decoder module may be configured to modify one or more parameters of the processing for a particular subject. For example, a decoder module may be configured to operate in a closed-loop system, wherein brain speech activity data is converted to speech feature data and output to an output device. The subject, or a non-subject user, may then interact with the decoder module to provide input as to the accuracy of the resulting output speech feature data. The decoder module may thus be configured to learn specific parameters to be applied in, for example, a linear spectrogram model and a non-linear modulation model; to learn which model(s) to apply; to learn which filter(s) to apply;

and the like. Such learning by the decoder module may comprise applying one or more statistical and/or machine learning algorithms, such as linear regression, principle component analysis, genetic algorithms, gradient boosting, neural networks, hidden Markov models, Bayesian networks, decision trees, and the like. In certain embodiments, the algorithms may use downsampling to reduce computational load. The algorithms may minimize overfitting (e.g., through cross validation, by limiting the number of learning iterations, etc.). A decoder module may thus be tailored for a particular subject.

The processor of the decoder module may further be configured to output the speech feature data to a data output component. In certain aspects, the data output component is configured to transmit speech feature data via direct physical communication (e.g., by a cable). For example, a data output component may include a cable that may be connected to a separate output device, as described below. An output component may also, or instead, transmit speech feature data by a non-physical means, such as wireless communication (e.g., Wi-Fi, cellular (e.g., 3G, 4G), Bluetooth and the like).

Output Devices

Once brain speech activity data is converted to speech feature data, it may be communicated to an output device. The phrase "output device" is intended to be used broadly and generically to refer to a device which may be used to display, processes, analyze, print, amplify, store, or utilize speech feature data. Illustrative but non-limiting examples of output devices may include a display monitor, a speaker, a phone (e.g., a smartphone) or a TTY device, a printer, a computer storage device (e.g. hard drive, tape drive, or other storage means), and other convenient output devices.

In certain aspects, a decoder and an output device may be separate devices. In other embodiments, a decoder and an output device may be the same device. For instance, a single device (e.g., a smartphone, or computer) may be used as both the decoder device and the output device.

The speech feature data that is output by the output device may include one or more phonemes, words, pseudowords (e.g., "heef" or "thack"), phrases, commands, actions, and/or sentences. In certain aspects, an output device may convert the speech feature data into readable text. The output device may output the readable text in a tangible (e.g., paper) or intangible form (e.g., a computer display). An output device may also, or instead, convert the speech feature data into audible sound. The audible sound may be played by the output device, such as by a speaker contained in the output device. In certain aspects, the output device may transmit the sound to a receiving device, which produces the audible sound. For instance, a smartphone may convert the speech feature data into audible sound that is transmitted to another phone, which produces the audible sound.

Systems

Also provided are systems for decoding brain speech activity of a subject into speech feature data. In certain aspects, the systems for decoding brain speech activity of a subject into speech feature data include a decoder device (e.g., as described above) having a data input component configured to receive brain speech activity data; a decoder module having a processor and a machine-readable medium encoding instructions operable to cause the processor to convert received brain speech activity data into speech feature data and output the speech feature data to an output component; and a data output component configured to output speech feature data from the decoder module.

A number of other components may also be included in systems of the present disclosure. In certain aspects, systems may include a brain speech activity acquisition device, which may receive brain speech activity from a subject. The brain speech activity acquisition device may be in operable communication with the data input component of the decoder, such as by wired and/or wireless communication. In some aspects, the brain speech activity acquisition device may include one or more electrodes, such as ECoG and/or EEG electrodes, such as are described herein.

Systems of the present disclosure may include one or more output devices. As described herein, examples of output devices of interest include, but are not limited to, a display monitor, a speaker, a phone (e.g., a smartphone) or a TTY device, a printer, a computer storage device (e.g. hard drive, tape drive, or other storage means), and other convenient output devices. The output device may output readable text in a tangible (e.g., paper) or intangible form (e.g., a computer display). An output device may also, or instead, convert the speech feature data into audible sound.

Utility

The subject methods and systems may be used to decode speech from brain activity data received from a subject. In many embodiments the subjects are "mammals" or "mammalian", where these terms are used broadly to describe organisms which are within the class mammalia, including primates (e.g., humans, chimpanzees, and monkeys). In many embodiments, the subjects are humans. The subject methods may be applied to human subjects of both genders and at any stage of development (i.e., fetal, neonates, infant, juvenile, adolescent, adult), where in certain embodiments the human subject is a juvenile, adolescent or adult. While the present invention may be applied to a human subject, it is to be understood that the subject methods may also be carried-out on other animal subjects (that is, in "non-human subjects").

Moreover, subjects of interest include those in which the ability to communicate via spoken language is lacking or impaired. Examples of such subjects include, but are not limited to, subjects who may be suffering from paralysis, locked-in syndrome, Lou Gehrig's disease, and/or other neurological diseases.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Those of skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Materials and Methods

The following are general materials and protocols used in the Examples below.

Participants and Neural Recordings

Electrocorticographic (ECoG) recordings were obtained using subdural electrode arrays implanted in 15 patients undergoing neurosurgical procedures for epilepsy or brain tumor. All participants volunteered and gave their informed consent before testing. The experimental protocol was approved by the Johns Hopkins Hospital, Columbia University Medical Center, University of California, San Francisco and Berkeley Institutional Review Boards and Committees on Human Research. Electrode grids had center-to-center distance of either 4 mm (N=4 participants) or 10 mm (N=11). Grid placement was determined entirely by clinical criteria and covered left or right fronto-temporal regions in all patients. Localization and coregistration of electrodes with the structural MRI is described in Dalal, et al. *Conf Proc IEEE Eng Med Biol Soc* 2007: 4941-4944; the disclosure of which is incorporated herein by reference. Multichannel ECoG data were amplified and digitally recorded with sampling rate=1,000 Hz (N=6 participants), 2,003 Hz (N=5), or 3,052 Hz (N=4). All ECoG signals were remontaged to a common average reference after removal of channels with artifacts or excessive noise (including electromagnetic noise from hospital equipment and poor contact with the cortical surface), as described by Crone, et al. (2001) *Clin Neurophysiol* 112: 565-582; the disclosure of which is incorporated herein by reference. Time-varying high gamma band power (70-150 Hz) was extracted from the multi-channel ECoG signal using the Hilbert-Huang transform as described by Canolty, et al. (2007) *Front Neurosci* 1: 185-196; the disclosure of which is incorporated herein by reference. It was then converted to standardized z-scores, and used for all analyses (except FIG. 6, Panel B in which the ECoG signal was filtered into 30 bands of width 10 Hz, ranging from 1-300 Hz, in order to calculate band-specific prediction accuracy). Data from a variety of language tasks were analyzed. Tasks included passive listening (N=5 participants), target word detection (N=5), and word/sentence repetition (N=5).

Speech Stimuli

Speech stimuli consisted of isolated words from a single speaker (N=10 participants) or sentences from a variety of male and female speakers (N=5). Isolated words included nouns, verbs, proper names, and pseudowords and were recorded by a native English female speaker (0.3-1 s duration, 16 kHz sample rate). Sentences were phonetically transcribed stimuli from the Texas Instruments/Massachusetts Institute of Technology (TIMIT) database (2-4 s, 16 kHz). Stimuli were presented aurally at the patient's bedside using either external free-field loudspeakers or calibrated ear inserts (Etymotic ER-5A) at approximately 70-80 dB.

The spectrogram representation (linear model) was generated from the speech waveform using a 128 channel auditory filter bank mimicking the auditory periphery. Filters had logarithmically spaced center frequencies ranging from 180-7,000 Hz and bandwidth of approximately $1/12^{th}$ octave. The spectrogram was subsequently downsampled to 32 frequency channels.

Figure 8:
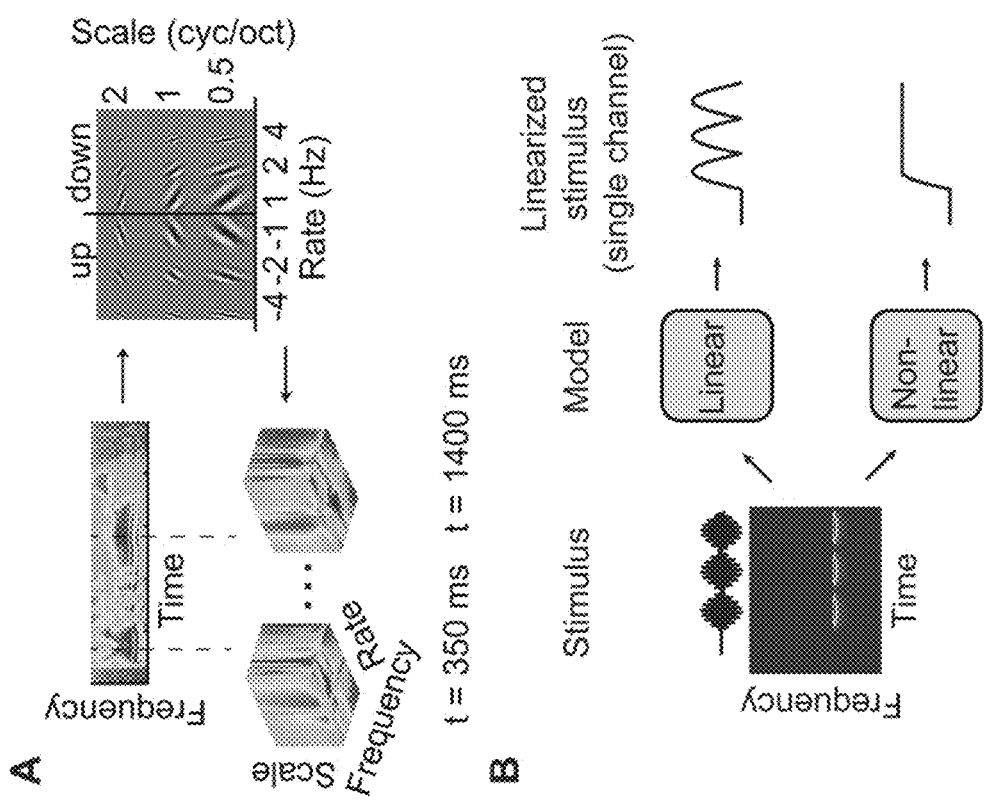
FIG. 8, Panels A-B show a schematic of a nonlinear modulation model. Panel A: The input spectrogram (top left) is transformed by a linear modulation filter bank (right) followed by a nonlinear magnitude operation. This nonlinear operation extracts the modulation energy of the incoming spectrogram and generates phase invariance to local fluctuations in the spectrogram envelope. The input representation is the two-dimensional spectrogram $S(f,t)$ across frequency f and time t. The output (bottom left) is the four-dimensional modulation energy representation $M(s,r,f,t)$ across spectral modulation scale s, temporal modulation rate r, frequency f, and time t. In the full modulation representation, negative rates by convention correspond to upward frequency sweeps, while positive rates correspond to downward frequency sweeps. Accuracy for positive and negative rates was averaged unless otherwise shown. Panel B: Schematic of linear (spectrogram envelope) and nonlinear (modulation energy) temporal coding. Left: acoustic waveform (black curve) and spectrogram of a temporally modulated tone. The linear spectrogram model (top) assumes that neural responses are a linear function of the spectrogram envelope (plotted for the tone center frequency channel, top right). In this case, the instantaneous output may be high or low and does not directly indicate the modulation rate of the envelope. The nonlinear modulation model (bottom) assumes that neural responses are a linear function of modulation energy. This is an amplitude-based coding scheme (plotted for the peak modulation channel, bottom right). The nonlinear modulation model explicitly estimates the modulation rate by taking on a constant value for a constant rate.
Figure 16:
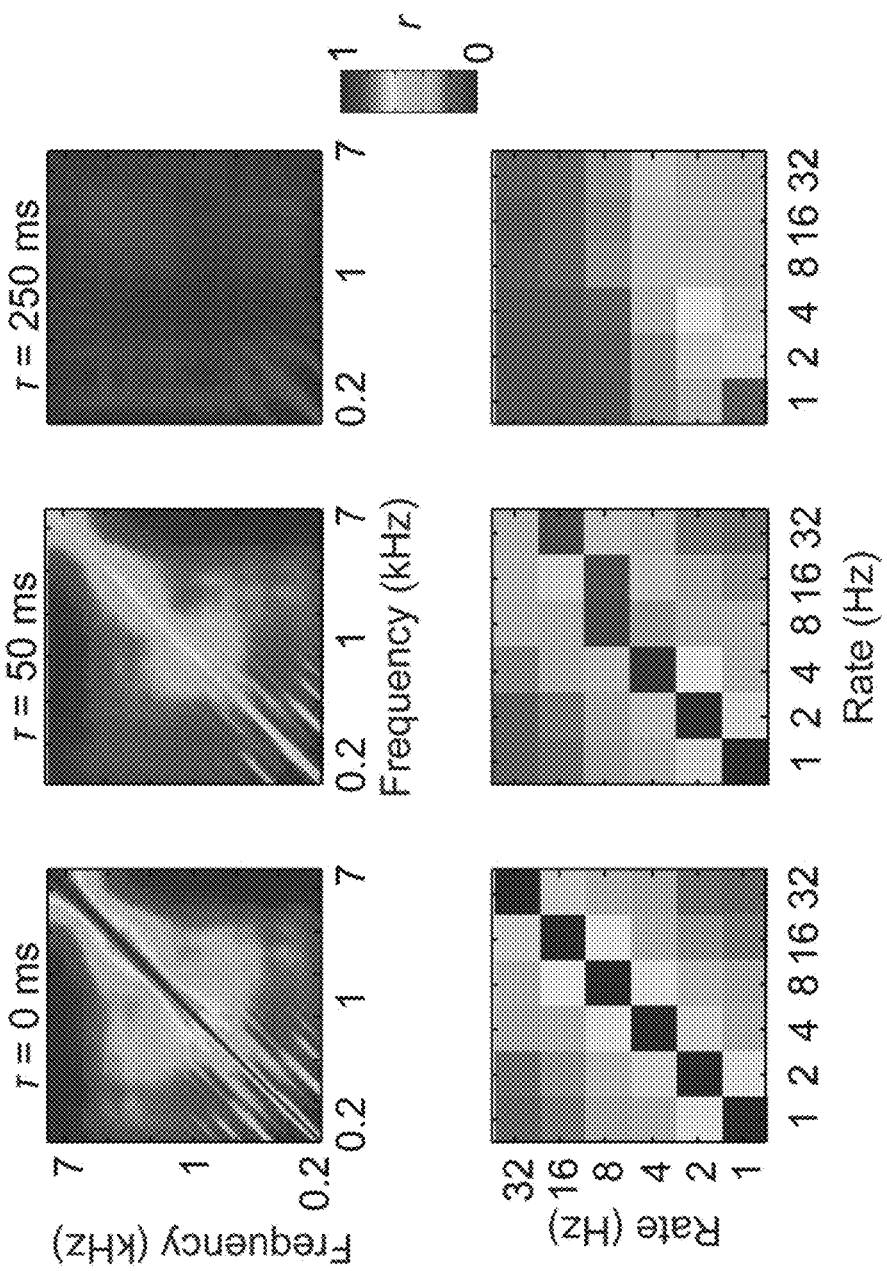
FIG. 16 shows stimulus correlations in linear and nonlinear stimulus representations. Speech, like other natural sounds, has strong stimulus correlations (illustrated for acoustic frequency, top panels, and temporal modulation rate, bottom panels). Correlations were estimated from 1,000 randomly selected TIMIT sentences at different time lags ($\tau$=0, 50, 250 ms; note the temporal asymmetry due to the use of causal modulation filters). Under an efficient coding hypothesis, these statistical redundancies may be exploited by the brain during sensory processing. An optimal linear estimator (Wiener filter) was used, which is essentially a multivariate linear regression and does not account for correlations among the output variables. Stimulus reconstruction therefore reflects an upper bound on the stimulus features that are encoded by the neural ensemble. The effect of stimulus statistics on reconstruction accuracy can be explored systematically using different stimulus priors.
Figure 17:
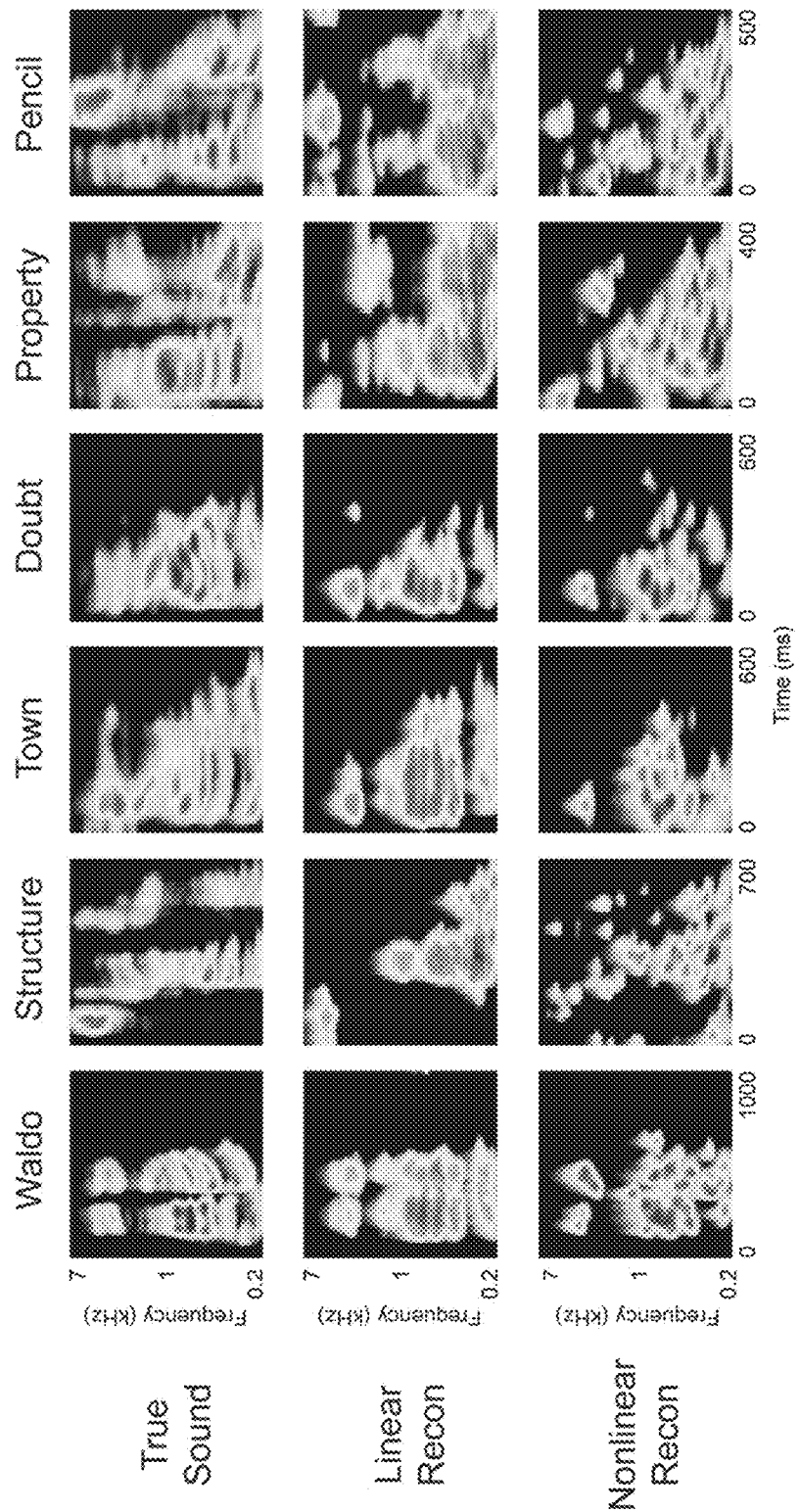
FIG. 17 shows the spectrograms of the original and reconstructed words. For audio playback, the spectrogram or modulation representations must be converted to an acoustic waveform, a transformation that requires both magnitude and phase information. Because the reconstructed representations are magnitude-only, the phase must be estimated. In general, this is known as the phase retrieval problem. To recover the acoustic waveform from the spectrogram, an iterative projection algorithm was used to estimate the phase. This step introduces additional acoustic artifacts that can distort the auditory features reconstructed directly from neural responses. Consequently, the audio file is an accurate but not perfect reflection of the reconstructed speech representation. A similar algorithm can be used to recover the spectrogram from the modulation representation. Here, the spectrogram reconstruction was projected into the (complex) modulation domain, the phase was extracted, and then the extracted phase was combined with the reconstructed magnitude of the modulation representation. With both phase and magnitude information, an invertible transformation can then be used to convert the (complex) modulation representation back to the spectrogram. Finally, to aid perceptual inspection of the reconstructions, the sample rate of the audio file is slightly slower (14 kHz) than that presented to participants (16 kHz).

The modulation representation (nonlinear model) was obtained by a 2-D complex wavelet transform of the 128 channel auditory spectrogram, implemented by a bank of causal modulation-selective filters spanning a range of spectral scales (0.5-8 cyc/oct) and temporal rates (1-32 Hz). The modulation selective filters are idealized spectro-temporal receptive fields similar to those measured in mammalian primary auditory cortex (FIG. 8, Panels A-B). The filter bank output constitutes a complex-valued time-varying multi-dimensional speech representation (downsampled to 32 acoustic frequency×12 rate×5 scale=1,920 total stimulus channels). The modulation representation is obtained by taking the magnitude of this complex-valued output. In specific analyses (stated in the text), reduced modulation representations were used to reduce dimensionality and to achieve an acceptable computational load, as well as to verify that tuning estimates were not affected by regularization, given the large number of fitted parameters in the full model. Reduced modulation representations included (1) rate-scale (60 total channels) and (2) rate only (six total channels). The rate-scale representation was obtained by averaging along the irrelevant dimension (frequency) prior to the nonlinear magnitude operation. The rate only representation was obtained by filtering the spectrogram with pure temporal modulation filters (described in Chi et al. (2005) *J Acoust Soc Am* 118: 887-90; the disclosure of which is incorporated herein by reference). Spectro-temporal filtering of the spectrogram is directional and captures upward and downward frequency sweeps, which by convention are denoted as positive and negative rates, respectively. Pure temporal filtering in the rate-only representation is not directional and results in half the total number of rate channels. These operations are described in Chi et al. FIG. 16 summarizes the stimulus correlations present in the linear and nonlinear representations.

Stimulus Reconstruction

The stimulus reconstruction model is the linear mapping between the responses at a set of electrodes and the original stimulus representation (e.g., modulation or spectrogram representation). For a set of N electrodes, the response of electrode n at time t=1 ... T was represented as R(t, n). The reconstruction model, $g(\tau, f, n)$, was a function that maps R(t, n) to stimulus S(t, f) as follows:

$$\hat{S}(t,f) = \Sigma_n \Sigma_\tau g(\tau, f, n) R(t-\tau, n) \quad (1)$$

where $\hat{S}$ denotes the estimated stimulus representation. Equation 1 implies that the reconstruction of each channel in the stimulus representation, $S_f(t)$, from the neural population is independent of the other channels (estimated using a separate set of $g_f(t, n)$). The reconstruction of one such channel can be written as:

$$\hat{S}_f(t) = \Sigma_n \Sigma_\tau g_f(\tau, n) R(t-\tau, n) \quad (2)$$

The entire reconstruction function was then described as the collection of functions for each stimulus feature:

$$G = \{g_1, g_2, \ldots g_F\} \quad (3)$$

For the spectrogram, time-varying spectral energy in 32 individual frequency channels was reconstructed. For the modulation representation, unless otherwise stated the reduced rate-scale representation was reconstructed, which consists of time-varying modulation energy in 60 rate-scale channels (defined in Speech Stimuli). $\tau$=100 temporal lags, discretized at 10 ms, was utilized.

Fitting

Prior to model fitting, stimuli and neural response data were synchronized, downsampled to 100 Hz, and standardized to zero mean and unit standard deviation. Model parameters (G in Eqn. 3) were fit to a training set of stimulus-response data (ranging from 2.5-17.5 min for different participants) using coordinate gradient descent with early stopping regularization, an iterative linear regression algorithm. Each data set was divided into training (80%), validation (10%), and test sets (10%). Overfitting was minimized by monitoring prediction accuracy on the validation set and terminating the algorithm after a series of 50 iterations failed to improve performance (an indication that overfitting was beginning to occur). Reconstruction accuracy was then evaluated on the independent test set. Coordinate descent produces a sparse solution in the weight vector (i.e., most weight values set to zero) and essentially performs variable selection simultaneously with model fitting. Consequently, there is no requirement to preselect electrodes for the reconstruction model. For grid sizes studied here, inclusion of all electrodes in the reconstruction model can be advantageous because the algorithm encourages irrelevant parameters to maintain zero weight, while allowing the model to capture additional variance using electrodes potentially excluded by feature selection approaches. Equal numbers of parameters are used to estimate each stimulus channel in both linear and nonlinear models. For each stimulus channel, the number of parameters in the corresponding reconstruction filter is N electrodes×100 time lags (the number of electrodes for each participant was determined by clinical criteria and therefore N varied by participant).

Cross-Validation

Parameter estimation was performed by a cross-validation procedure using repeated random subsampling. For each repeat, trials were randomly partitioned into training (80% of trials), validation (10%), and test sets (10%); model fitting was then performed using the training/validation data; and reconstruction accuracy was evaluated on the test set. This procedure was repeated multiple times (depending on computational load) and the parameters and reconstruction accuracy measures were averaged over all repeats. The forward encoding models were estimated using 20 resamples; the spectrogram and modulation reconstruction models were estimated using 10 and 3 resamples, respectively (due to increasing computational load). Identical data partitions were used for comparing predictive power for different reconstruction models (i.e., spectrogram versus modulation) to ensure potential differences were not due to different stimuli or noise levels in the evaluation data. To check stability of the generalization error estimates, it was verified that estimated spectrogram reconstruction accuracy was stable as a function of the number of resamples used in the estimation (ranging from 3 to 10). The total duration of the test set equaled the length of the concatenated resampled data sets (range of ~0.8-17.5 min across participants). Standard error of individual parameters was calculated as the standard deviation of the resampled estimates. Statistical significance of individual parameters was assessed by the t-ratio (coefficient divided by its resampled standard error estimate). Model fitting was performed with the MATLAB toolbox STRFLab.

Reconstruction Accuracy

Reconstruction accuracy was quantified separately for each stimulus component by computing the correlation coefficient (Pearson's r) between the reconstructed and original stimulus component. For each participant, this yielded 32 individual correlation coefficients for the 32 channel spectrogram model and 60 correlation coefficients for the 60 channel rate-scale modulation model (defined in Speech Stimuli). Overall reconstruction accuracy is reported as the mean correlation over all stimulus components.

To make a direct comparison of modulation and spectrogram-based accuracy, the reconstructions need to be compared in the same stimulus space. The linear spectrogram reconstruction was therefore projected into the rate-scale modulation space (using the modulation filter bank as described in Speech Stimuli). This transformation provides an estimate of the modulation content of the spectrogram reconstruction and allows direct comparison with the modulation reconstruction. The transformed reconstruction was then correlated with the 60 rate-scale components of the original stimulus. Accuracy as a function of rate (FIG. 7, Panel A) was calculated by averaging over the scale dimension. Positive and negative rates were also averaged unless otherwise shown. Comparison of reconstruction accuracy for a subset of data in the full rate-scale-frequency modulation space yielded similar results. To impose additivity and approximate a normal sampling distribution of the correlation coefficient statistic, Fisher's z-transform was applied to correlation coefficients prior to tests of statistical significance and prior to averaging over stimulus channels and participants. The inverse z-transform was then applied for all reported mean r values.

Figure 9:
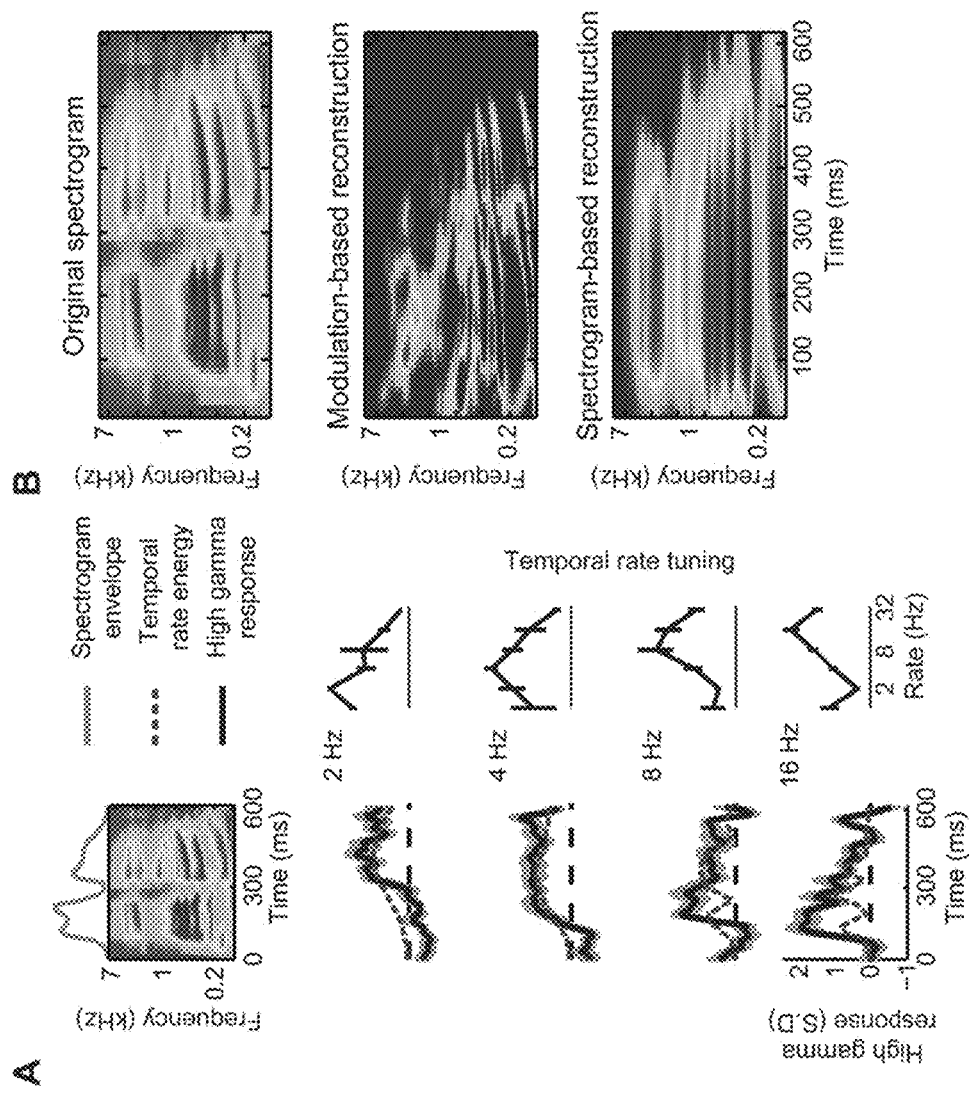
FIG. 9, Panels A-B depict an example of nonlinear modulation coding and reconstruction. Panel A: Top: the spectrogram of an isolated word ("waldo") presented aurally to one participant. Blue curve plots the spectrogram envelope, summed over all frequencies. Left panels: induced high gamma responses (black curves, trial averaged) at four different STG sites. Temporal modulation energy of the stimulus (dashed red curves) is overlaid (computed from 2, 4, 8, and 16 Hz modulation filters and normalized to maximum value). Dashed black lines indicate baseline response level. Right panels: nonlinear modulation rate tuning curves for each site (estimated from nonlinear STRFs). Shaded regions and error bars indicate SEM. Panel B: Original spectrogram (top), modulation-based reconstruction (middle), and spectrogram-based reconstruction (bottom), linearly decoded from a fixed set of STG electrodes. The modulation reconstruction is projected into the spectrogram domain using an iterative projection algorithm and an overcomplete set of modulation filters. The displayed spectrogram is averaged over 100 random initializations of the algorithm.

To visualize the modulation-based reconstruction in the spectrogram domain (FIG. 9, Panel B), the 4-D modulation representation needs to be inverted. If both magnitude and phase responses are available, the 2-D spectrogram can be restored by a linear inverse filtering operation. Here, only the magnitude response is reconstructed directly from neural activity. In this case, the spectrogram can be recovered approximately from the magnitude-only modulation representation using an iterative projection algorithm and an overcomplete set of modulation filters as described in Chi et al. FIG. 9, Panel B displays the average of 100 random initializations of this algorithm. This approach is subject to non-neural errors due to the phase-retrieval problem (i.e., the algorithm does not perfectly recover the spectrogram, even when applied to the original stimulus). Therefore, quantitative comparisons with the spectrogram-based reconstruction were performed in the modulation space.

Reconstruction accuracy was cross-validated and the reported correlation is the average over all resamples (see Cross-Validation). Standard error was computed as the standard deviation of the resampled distribution. The reported correlations are not corrected to account for the noise ceiling on prediction accuracy, which limits the amount of potentially explainable variance. An ideal model would not achieve perfect prediction accuracy of r=1.0 due to the presence of random noise that is unrelated to the stimulus. With repeated trials of identical stimuli, it is possible to estimate trial-to-trial variability to correct for the amount of potentially explainable variance. A sufficient number of trial repetitions (>5) was generally unavailable for a robust estimate, and uncorrected values are therefore reported.

STRF Encoding Models

Encoding models describe the linear mapping between the stimulus representation and the neural response at individual sites. For a stimulus representation s(x,t) and instantaneous neural response r(t) sampled at times t=1 ... T, the encoding model is defined as the linear mapping:

$$r(t) = \sum_{\substack{x=1, \\ u=0}}^{X,U} h(x,u)s(x, t-u) + e(t). \quad (4)$$

Each coefficient of h indicates the gain applied to stimulus feature x at time lag u. Positive values indicate components of the stimulus correlated with increased neural response, and negative values indicate components correlated with decreased response. The residual, e(t), represents components of the response (nonlinearities and noise) that cannot be predicted by the encoding model.

Model fitting for the STRF models (h in Eqn. 4) proceeded similarly to reconstruction except a standard gradient descent algorithm (with early stopping regularization) was used that does not impose a sparse solution. The linear STRF model included 32 frequency channels×100 time lags (3,200 parameters). The full nonlinear modulation STRF model included 32 frequency×5 scale×12 rate×100 time lags (192,000 parameters) and the reduced rate-time modulation model (FIG. 14, Panels A-B) included 6 rate×100 time lags (600 parameters). The STRF models were cross-validated using 20 resampled data sets with no overlap between training and test partitions within each resample. Data partitions were identical across STRF model type (linear and nonlinear). Identical resampled data sets for estimating STRF and reconstruction models were not enforced, because the predictive power of these two approaches is not comparable. Tuning curves were estimated from STRFs as follows: Frequency tuning was estimated from the linear STRF models by first setting all inhibitory weights to zero and then summing across the time dimension. Nonlinear rate tuning was estimated from the nonlinear STRF modulation model by the same procedure, using the reduced rate-only representation. Linear rate tuning was estimated from the linear STRF model by filtering the fitted STRF with the modulation filter bank (see Speech Stimuli) and averaging along the irrelevant dimensions. Linear rate tuning computed in this way was similar to that computed from the modulation transfer function (modulus of the 2-D Fourier transform) of the fitted linear STRF. For all tuning curves, standard error was computed as the standard deviation of the resampled estimates. Frequency tuning curve peaks were identified as significant parameters ($t > 2.0$) separated by more than a half octave. To calculate ensemble tuning curves (FIG. 7, Panel B), the tuning curve for each site was normalized by the maximum value and averaged across sites. STG sites with forward prediction accuracy of $r > 0.1$ were analyzed (n=195).

Example 1: Reconstruction of Heard Speech from Brain Activity

Figure 4:
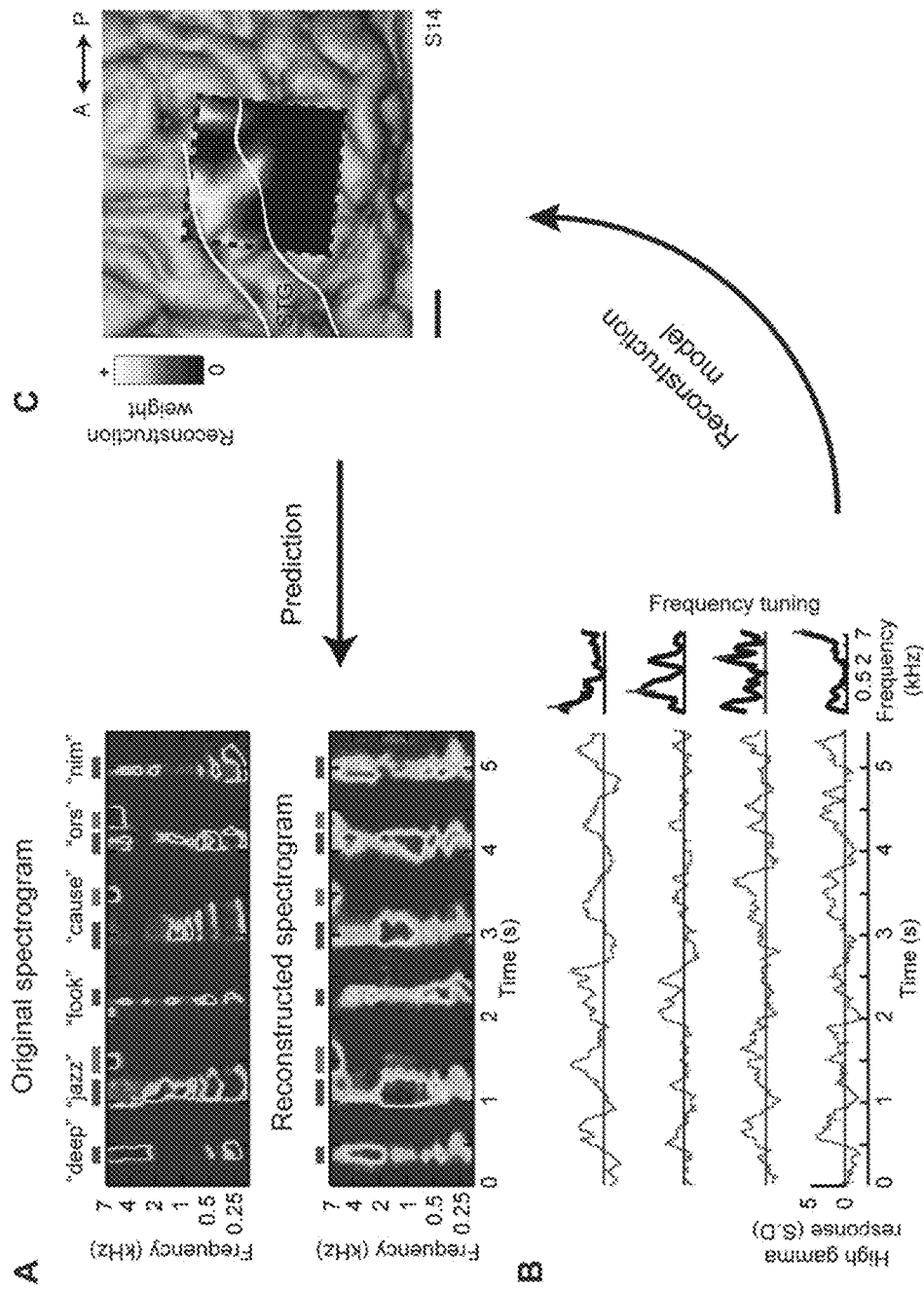
FIG. 4, Panels A-C depict spectrogram reconstruction. Panel A: The top panel shows spectrogram of six isolated words (deep, jazz, cause) and pseudowords (fook, ors, nim) presented aurally to an individual participant. (Bottom): spectrogram-based reconstruction of the same speech segment, linearly decoded from a set of electrodes. Dark gray and light gray bars denote vowels and fricative consonants, respectively, and the spectrogram is normalized within each frequency channel for display. Panel B: Single trial high gamma band power (70-150 Hz, gray curves) induced by the speech segment in Panel A. Recordings are from four different STG sites used in the reconstruction. The high gamma response at each site is z-scored and plotted in standard deviation (SD) units. Right panel: frequency tuning curves (dark black) for each of the four electrode sites, sorted by peak frequency and normalized by maximum amplitude. Red bars overlay each peak frequency and indicate SEM of the parameter estimate. Frequency tuning was computed from spectro-temporal receptive fields (STRFs) measured at each individual electrode site. Tuning curves exhibit a range of functional forms including multiple frequency peaks (FIG. 11, Panel B and FIG. 12, Panel B). Panel C: The anatomical distribution of fitted weights in the reconstruction model. Dashed box denotes the extent of the electrode grid (shown in FIG. 3). Weight magnitudes are averaged over all time lags and spectrogram frequencies and spatially smoothed for display. Nonzero weights are largely focal to STG electrode sites. Scale bar is 10 mm.

Words and sentences from different English speakers were presented aurally to 15 patients undergoing neurosurgical procedures for epilepsy or brain tumor. All patients had normal language capacity as determined by neurological exam. Cortical surface field potentials were recorded from non-penetrating multi-electrode arrays placed over the lateral temporal cortex (FIG. 3, dark gray circles), including the pSTG. The nature of auditory information contained in temporal cortex neural responses was investigated using a stimulus reconstruction approach (see Materials and Methods, above). The reconstruction procedure was a multi-input, multi-output predictive model that was fit to stimulus-response data. It constitutes a mapping from neural responses to a multi-dimensional stimulus representation (FIGS. 3 and 4, Panels A-C). This mapping can be estimated using a variety of different learning algorithms, as described by Hastie, et al. (2009) Elements of statistical learning, the disclosure of which is incorporated by reference. New York, N.Y.: Springer Science; the disclosure of which is incorporated herein by reference. A regularized linear regression algorithm was used to minimize the mean-square error between the original and reconstructed stimulus. Once the model was fit to a training set, it could then be used to predict the spectro-temporal content of any arbitrary sound, including novel speech not used in training.

A key component in the reconstruction algorithm was the choice of stimulus representation. Previous applications of stimulus reconstruction in non-human auditory systems have focused primarily on linear models to reconstruct the auditory spectrogram. The spectrogram is a time-varying representation of the amplitude envelope at each acoustic frequency (FIG. 3, bottom left). The spectrogram envelope of natural sounds is not static but rather fluctuates across both frequency and time. Envelope fluctuations in the spectrogram are referred to as modulations and play an important role in the intelligibility of speech. Temporal modulations occur at different temporal rates and spectral modulations occur at different spectral scales. For example, slow and intermediate temporal modulation rates (<4 Hz) are associated with syllable rate, while fast modulation rates (>16 Hz) correspond to syllable onsets and offsets. Similarly, broad spectral modulations relate to vowel formants while narrow spectral structure characterizes harmonics. In the linear spectrogram model, modulations are represented implicitly as the fluctuations of the spectrogram envelope. Furthermore, neural responses are assumed to be linearly related to the spectrogram envelope.

For stimulus reconstruction, the linear spectrogram model was first applied to human pSTG responses using a stimulus set of isolated words from an individual speaker. A leave-one-out cross-validation fitting procedure was used in which the reconstruction model was trained on stimulus-response data from isolated words and evaluated by directly comparing the original and reconstructed spectrograms of the out-of-sample word. Reconstruction accuracy was quantified as the correlation coefficient (Pearson's r) between the original and reconstructed stimulus. The reconstruction procedure is illustrated in FIG. 4, Panels A-C for one participant with a high-density (4 mm) electrode grid placed over posterior temporal cortex. For different words, the linear model yielded accurate spectrogram reconstructions at the level of single trial stimulus presentations (FIG. 4, Panels A-C, and 17). The reconstructions captured major spectro-temporal features such as energy concentration at vowel harmonics (FIG. 4, Panel A, dark gray bars) and high frequency components during fricative consonants (FIG. 4, Panel A, [z] and [s], lighter gray bars). The anatomical distribution of weights in the fitted reconstruction model revealed that the most informative electrode sites within temporal cortex were largely confined to pSTG (FIG. 4, Panel C).

Figure 5:
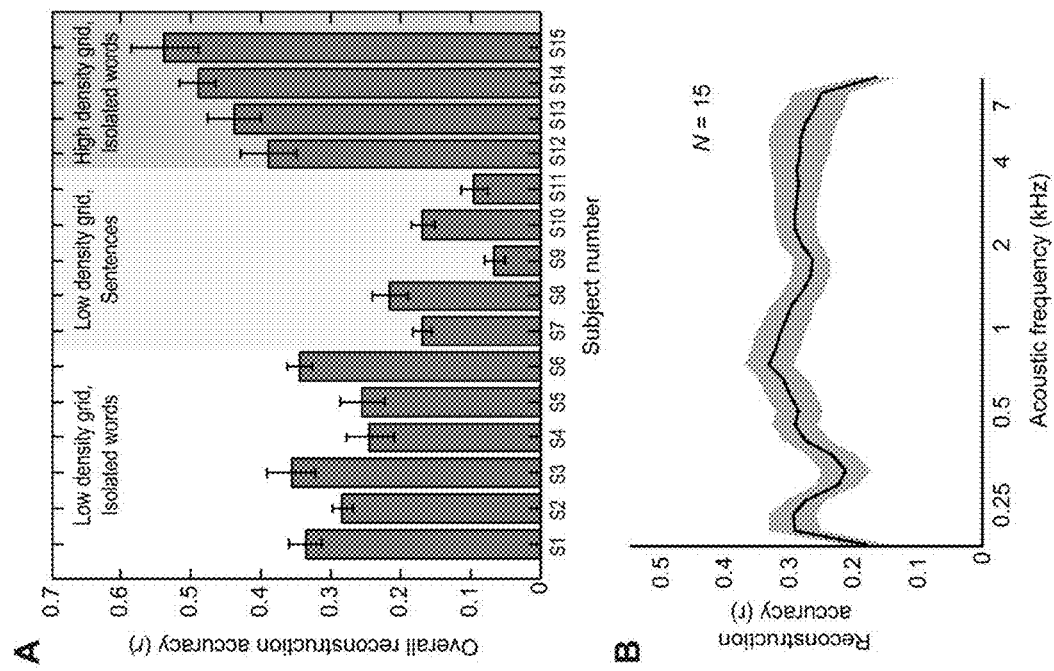
FIG. 5, Panels A-B show individual participant and group average reconstruction accuracy. Panel A: Overall reconstruction accuracy for each participant using the linear spectrogram model. Error bars denote resampling SEM. Overall accuracy is reported as the mean over all acoustic frequencies. Participants are grouped by grid density (low or high) and stimulus set (isolated words or sentences). Statistical significance of the correlation coefficient for each individual participant was computed using a randomization test. Reconstructed trials were randomly shuffled 1,000 times and the correlation coefficient was computed for each shuffle to create a null distribution of coefficients. The p value was calculated as the proportion of elements greater than the observed correlation. Panel B: Reconstruction accuracy as a function of acoustic frequency averaged over all participants (N=15) using the linear spectrogram model. Shaded region denotes SEM over participants.

Across the sample of participants (N=15), cross-validated reconstruction accuracy for single trials was significantly greater than zero in all individual participants ($p < 0.001$, randomization test, FIG. 5, Panel A). At the population level, mean accuracy averaged over all participants and stimulus sets (including different word sets and continuous sentences from different speakers) was highly significant (mean accuracy $r=0.28$, $p<10^{-5}$, one-sample Nest, df=14). As a function of acoustic frequency, mean accuracy ranged from $r=\sim 0.2$-$0.3$ (FIG. 5, Panel B).

Figure 6:
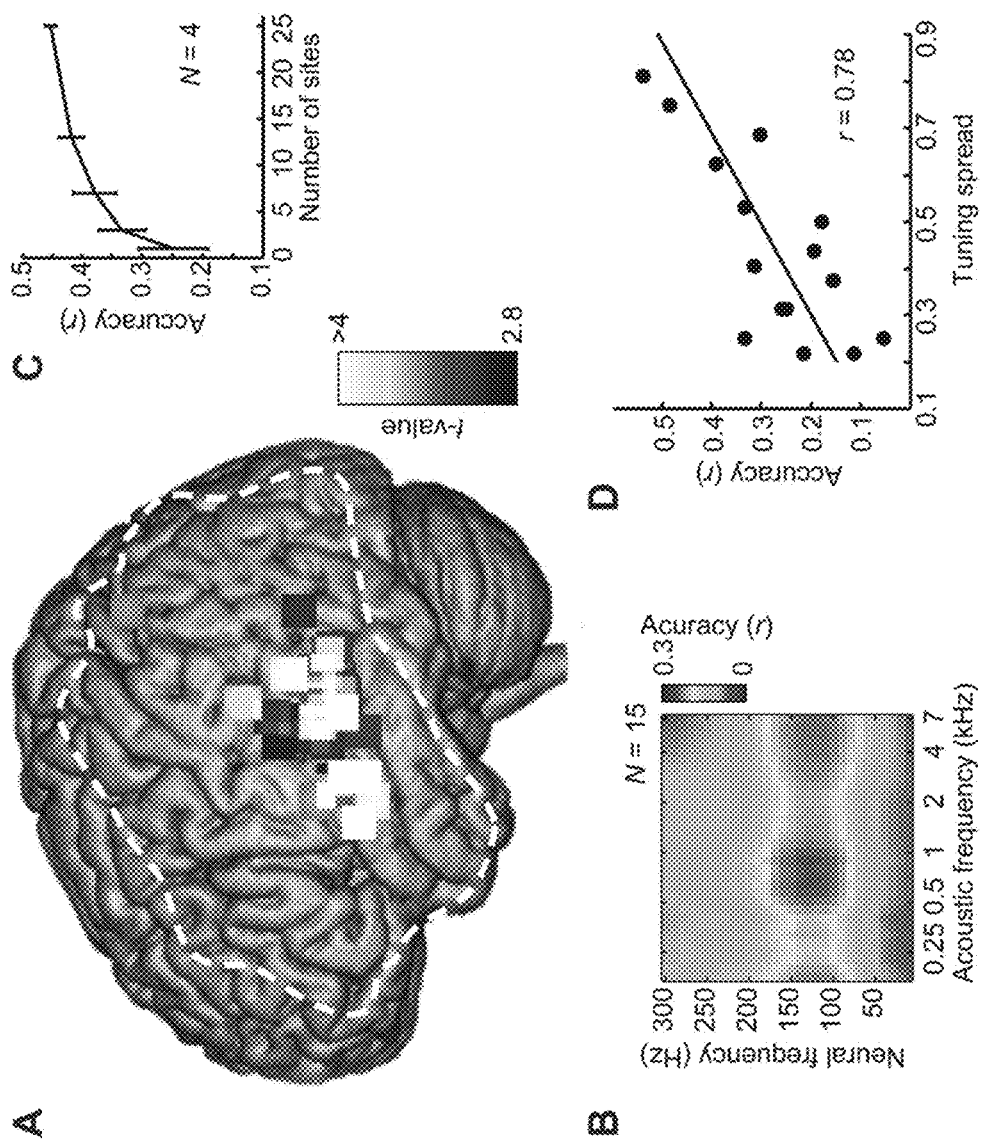
FIG. 6, Panels A-D show factors influencing reconstruction quality. Panel A: Group average t value map of informative electrodes, which are predominantly localized to posterior STG. For each participant, informative electrodes are defined as those associated with significant weights ($p<0.05$, FDR correction) in the fitted reconstruction model. To plot electrodes in a common anatomical space, spatial coordinates of significant electrodes are normalized to the MNI (Montreal Neurological Institute) brain template (Yale BioImage Suite). The dashed white line denotes the extent of electrode coverage pooled over participants. Panel B: Reconstruction accuracy is significantly greater than zero when using neural responses within the high gamma band (~70-170 Hz; $p<0.05$, one sample t tests, df=14, Bonferroni correction). Accuracy was computed separately in 10 Hz bands from 1-300 Hz and averaged across all participants (N=15). Panel C: Mean reconstruction accuracy improves with increasing number of electrodes used in the reconstruction algorithm. Error bars indicate SEM over 20 cross-validated data sets of four participants with 4 mm high density grids. Panel D: Accuracy across participants is strongly correlated ($r=0.78$, $p<0.001$, df=13) with tuning spread (which varied by participant depending on grid placement and electrode density). Tuning spread was quantified as the fraction of frequency bins that included one or more peaks, ranging from 0 (no peaks) to 1 (at least one peak in all frequency bins, ranging from 180-7,000 Hz).

Second, significant predictive power ($r > 0$) was largely confined to neural responses in the high gamma band (~70-170 Hz; FIG. 6, Panel B; $p < 0.01$, one-sample t tests, df=14, Bonferroni correction). Predictive power for the high gamma band (~70-170 Hz) was significantly better compared to other neural frequency bands ($p < 0.05$, Bonferroni adjusted pair-wise comparisons between frequency bands, following significant one-way repeated measures analysis of variance (ANOVA), $F(30,420)=128.7$, $p<10^{-10}$).

Third, increasing the number of electrodes used in the reconstruction improved overall reconstruction accuracy (FIG. 6, Panel C). Overall prediction quality was relatively low for participants with five or fewer responsive STG electrodes (mean accuracy r=0.19, N=6 participants) and was robust for cases with high density grids (mean accuracy r=0.43, N=4, mean of 37 responsive STG electrodes per participant).

Figure 12:
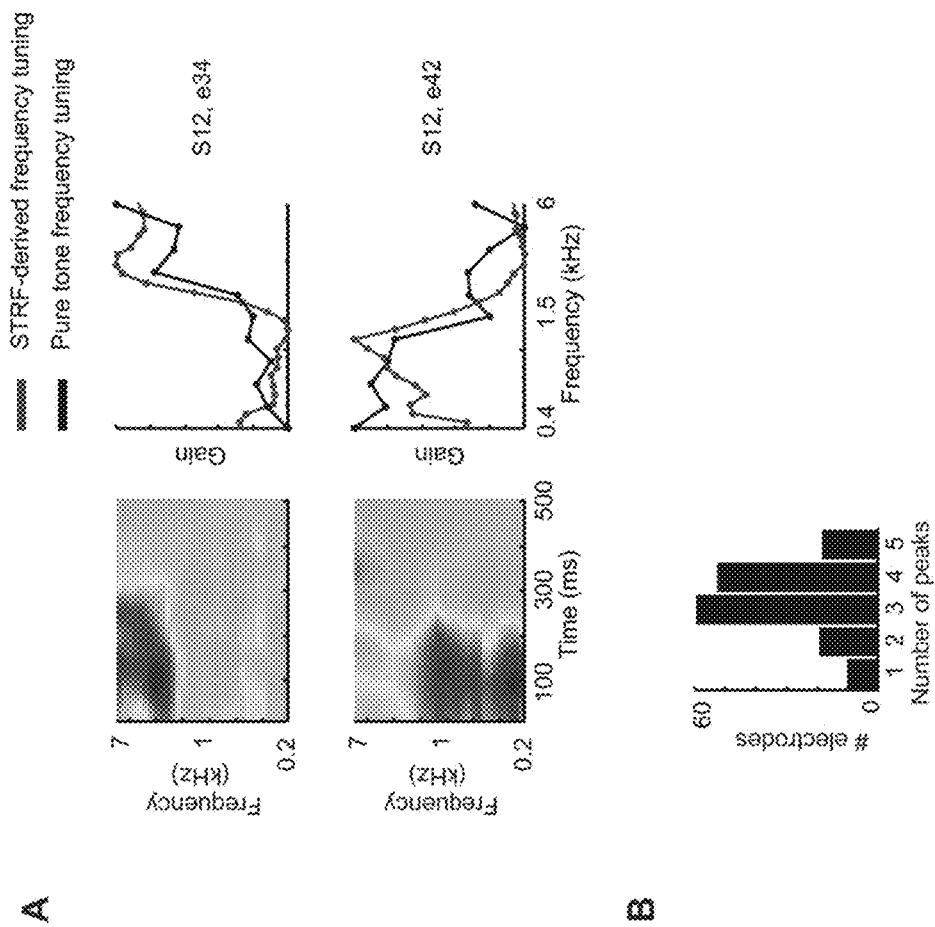
FIG. 12, Panels A-B depict frequency tuning. Panel A: Left panels: linear STRFs for two example electrode sites. Right panels: pure tone frequency tuning (black curves) matches frequency tuning derived from fitted linear STRF models (red curves). For one participant, pure tones (375-6,000 Hz, logarithmically spaced) were presented for 100 ms at 80 dB. Pure tone tuning curves were calculated as the amplitudes of the induced high gamma response across tone frequencies. STRF-derived tuning curves were calculated by first setting all inhibitory weights to zero and then summing across the time dimension. At these two sites, frequency tuning is approximately high-pass (top) or low-pass (bottom). Panel B: Distribution of the number of frequency tuning peaks across significant electrodes (N=15 participants) estimated from linear STRF models (32-channel). The majority of sites exhibit complex frequency tuning patterns of 2-5 peaks. Peaks were identified as significant parameters (t>2.0) separated by more than a half octave.

Certain neural response properties were identified that allow the linear model to find an effective mapping to the stimulus spectrogram. For example, individual recording sites should preferably exhibit reliable frequency selectivity (e.g., FIG. 4, Panel B, right column; FIG. 11, Panel B; FIG. 12, Panels A-B). An absence of frequency selectivity (i.e., equal neural response amplitudes to all stimulus frequencies) would imply that neural responses do not encode frequency and could not be used to differentiate stimulus frequencies. To quantify frequency tuning at individual electrodes, estimates of standard spectro-temporal receptive fields (STRFs) were used. The STRF is a forward modeling approach commonly used to estimate neural tuning to a wide variety of stimulus parameters in different sensory systems. It was found that different electrodes were sensitive to different acoustic frequencies important for speech sounds, ranging from low (~200 Hz) to high (~7,000 Hz). The majority of individual sites exhibited a complex tuning profile with multiple peaks (e.g., FIG. 4, Panel B, rows 2 and 3; FIG. 12, Panel B). The full range of the acoustic speech spectrum was encoded by responses from multiple electrodes in the ensemble, although coverage of the spectrum varied by participant (FIG. 6, Panel B). Across participants, total reconstruction accuracy was positively correlated with the proportion of spectrum coverage (r=0.78, p<0.001, df=13; FIG. 6, Panel D).

Figure 7:
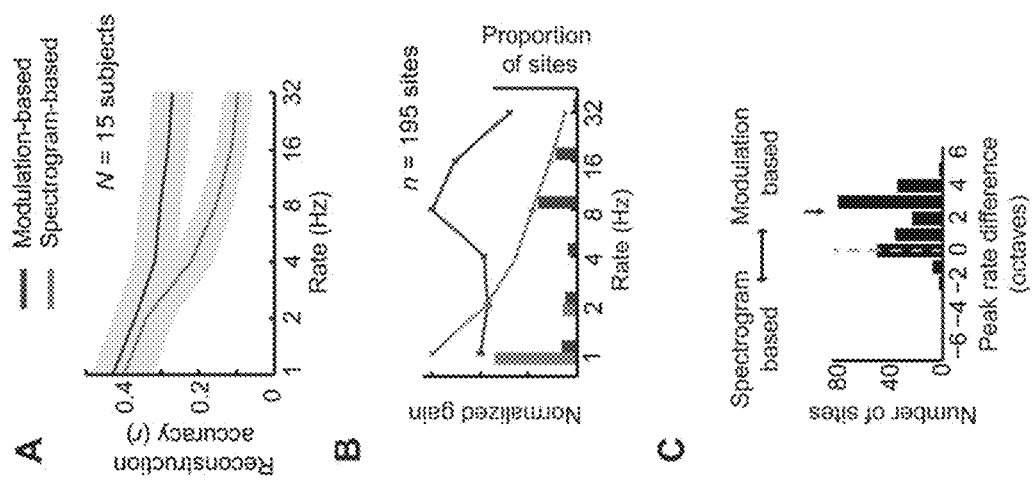
FIG. 7, Panels A-C compare linear and nonlinear coding of temporal fluctuations. Panel A: Mean reconstruction accuracy (r) as a function of temporal modulation rate, averaged over all participants (N=15). Modulation-based decoding accuracy (red curve) is higher compared to spectrogram-based decoding (blue curve) for temporal rates ≥4 Hz. In addition, spectrogram-based decoding accuracy is significantly greater than zero for lower modulation rates (≤8 Hz), supporting the possibility of a dual modulation and envelope-based coding scheme for slow modulation rates. Shaded gray regions indicate SEM over participants. Panel B: Mean ensemble rate tuning curve across all predictive electrode sites (n=195). Error bars indicate SEM. Overlaid histograms indicate proportion of sites with peak tuning at each rate. Panel C: Within-site differences between modulation and spectrogram-based tuning. Arrow indicates the mean difference across sites. Within-site, nonlinear modulation models are tuned to higher temporal modulation rates than the corresponding linear spectrogram models ($p<10^{-7}$, two sample paired t test, df=194).

Further, the neural response should preferably rise and fall reliably with fluctuations in the stimulus spectrogram envelope. This is because the linear model assumes a linear mapping between the response and the spectrogram envelope. This requirement for "envelope-locking" reveals a major limitation of the linear model, which is most evident at fast temporal modulation rates. This limitation is illustrated in FIG. 7, Panel A (blue curve), which plots reconstruction accuracy as a function of modulation rate. A one-way repeated measures ANOVA (F(5,70)=13.99, p<10$^{-8}$) indicated that accuracy was significantly higher for slow modulation rates (≤4 Hz) compared to faster modulation rates (>8 Hz) (p<0.05, post hoc pair-wise comparisons, Bonferroni correction). Accuracy for slow and intermediate modulation rates (≤8 Hz) was significantly greater than zero (r=~0.15 to 0.42; one-sample paired t tests, p<0.0005, df=14, Bonferroni correction) indicating that the high gamma response faithfully tracks the spectrogram envelope at these rates. However, accuracy levels were not significantly greater than zero at fast modulation rates (>8 Hz; r=~0.10; one-sample paired Nests, p>0.05, df=14, Bonferroni correction), indicating a lack of reliable envelope-locking to rapid temporal fluctuations.

Given the failure of the linear spectrogram model to reconstruct fast modulation rates, competing models of auditory neural encoding were evaluated. An alternative, nonlinear model based on modulation (described in Chi, et al.) was investigated. Speech sounds are characterized by both slow and fast temporal modulations (e.g., syllable rate versus onsets) as well as narrow and broad spectral modulations (e.g., harmonics versus formants). The modulation model represents these multi-resolution features explicitly through a complex wavelet analysis of the auditory spectrogram. Computationally, the modulation representation is generated by a population of modulation-selective filters that analyze the two-dimensional spectrogram and extract modulation energy (a nonlinear operation) at different temporal rates and spectral scales (FIG. 8, Panel A). Conceptually, this transformation is similar to the modulus of a 2-D Fourier transform of the spectrogram, localized at each acoustic frequency.

The nonlinear component of the model is phase invariance to the spectrogram envelope (FIG. 8, Panel B). A fundamental difference with the linear spectrogram model is that phase invariance permits a nonlinear temporal coding scheme, whereby envelope fluctuations are encoded by amplitude rather than envelope-locking (FIG. 8, Panel B). Such amplitude-based coding schemes are broadly referred to as "energy models." The modulation model therefore represents an auditory analog to the classical energy model of complex cells in the visual system, which are invariant to the spatial phase of visual stimuli.

Figure 13:
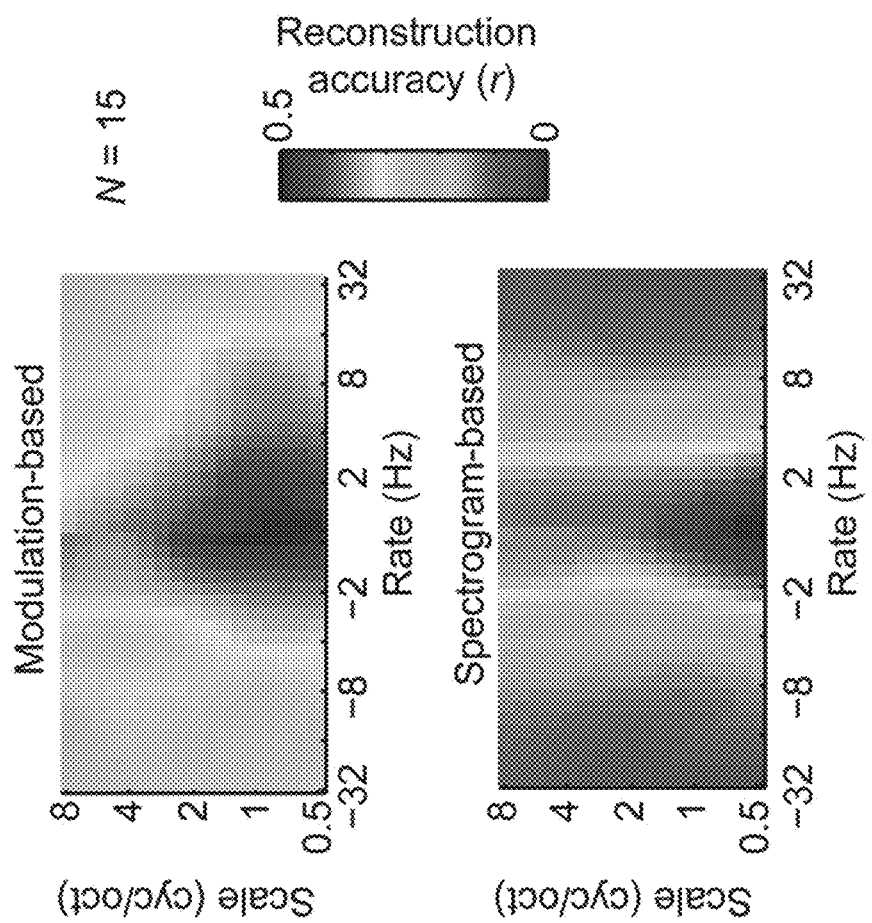
FIG. 13 shows mean reconstruction accuracy for the joint rate-scale space across all participants (N=15). Top: modulation-based (nonlinear) decoding accuracy is significantly higher compared to frequency-based (linear) decoding (bottom) for all spectral scales at temporal rates $\geq 16$ Hz ($p<0.05$, post hoc pair-wise comparisons, Bonferroni correction, following significant two-way repeated measures ANOVA; model type by stimulus component interaction effect, $F(59, 826)=1.84$, $p<0.0005$).

Reconstructing the modulation representation proceeds similarly to the spectrogram, except that individual reconstructed stimulus components now correspond to modulation energy at different rates and scales instead of spectral energy at different acoustic frequencies. Next, reconstruction accuracy was compared using the nonlinear modulation model to that of the linear spectrogram model (FIG. 7, Panel A; FIG. 13). In the group data, the nonlinear model yielded significantly higher accuracy compared to the linear model (two-way repeated measures ANOVA; main effect of model type, F(1,14)=33.36, p<10$^{-4}$). This included significantly better accuracy for fast temporal modulation rates compared to the linear spectrogram model (4-32 Hz; FIG. 7, Panel A, red versus blue curves; model type by modulation rate interaction effect, F(5,70)=3.33, p<0.01; post hoc pair-wise comparisons, p<10$^{-4}$, Bonferroni correction).

Figure 14:
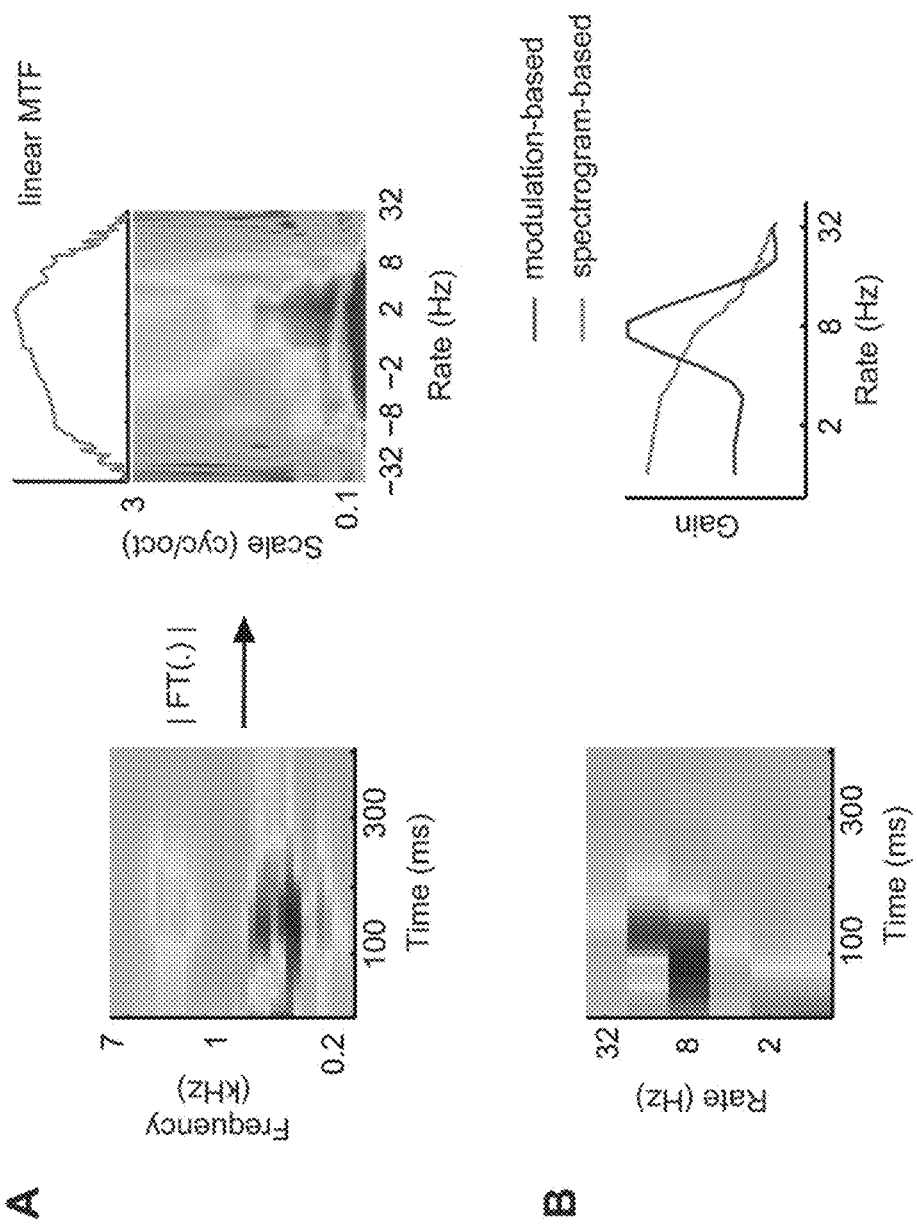
FIG. 14, Panels A-B show modulation rate tuning was estimated from both linear and nonlinear STRF models, based on the spectrogram or modulation representation, respectively. Linear STRFs have a 2-D parameter space (frequency×time). Modulation rate tuning for the linear STRF was computed by filtering the fitted STRF model with the modulation filter bank and averaging along the irrelevant dimensions. Modulation rate tuning computed in this way was similar to that computed from the modulation transfer function (MTF) (modulus of the 2-D Fourier transform of the fitted STRF). Nonlinear STRFs have a 4-D parameter space (rate×scale×frequency×time). Modulation-based rate tuning curves were computed by summing across the three irrelevant dimensions. Modulation rate tuning was similar whether this procedure was applied to a reduced dimension model (rate×time only) or to the marginalized full model. Reported estimates of modulation rate tuning were computed from the reduced (rate×time) models. Panel A: Left: example linear STRF. The linear STRF can be transformed into rate-scale space (the MTF, right) by taking the modulus of the 2-D Fourier transform or by filtering the STRF with the modulation filter bank. The linear modulation rate tuning curve (blue curve, top) is obtained after averaging along the scale dimension. Panel B: Left: example nonlinear STRF from the same site as in Panel A, fit in the rate-time parameter space. Right: the corresponding modulation-based rate tuning curve (red) is plotted against the spectrogram-based tuning curve (blue) from Panel A (only positive rates are shown).

The improved performance of the modulation model suggested that this representation provided better neural sensitivity to fast modulation rates compared to the linear spectrogram. To further investigate this possibility, modulation rate tuning curves at individual STG electrode sites (n=195) were estimated using linear and nonlinear STRFs, which are based on the spectrogram and modulation representations, respectively (FIG. 14, Panels A-B). The average envelope-locked responses exhibit prominent tuning to low rates (1-8 Hz) with a gradual loss of sensitivity at higher rates (>8 Hz) (FIG. 7, Panels B-C). In contrast, the average modulation-based tuning curves preserve sensitivity to much higher rates approaching 32 Hz (FIG. 7, Panels B-C).

Sensitivity to fast modulation rates at single STG electrodes is illustrated for one participant in FIG. 9, Panel A. In this example (the word "waldo"), the spectrogram envelope (blue curve, top) fluctuates rapidly between the two syllables ("wal" and "do," ~300 ms). The linear model assumes that neural responses (high gamma power, black curves, left) are envelope-locked and directly track this rapid change. However, robust tracking of such rapid envelope changes was not generally observed, in violation of linear model assumptions. This is illustrated for several individual electrodes in FIG. 9, Panel A (compare black curves, left, with blue curve, top). In contrast, the modulation representation encodes this fluctuation nonlinearly as an increase in energy at fast rates (>8 Hz, dashed red curves, ~300 ms, bottom two rows). This allows the model to capture energy-based modulation information in the neural response. Modulation energy encoding at these sites is quantified by the corresponding nonlinear rate tuning curves (FIG. 9, Panel A, right column). These tuning curves show neural sensitivity to a range of temporal modulations with a single peak rate. For illustrative purposes, FIG. 9, Panel A (left) compares modulation energy at the peak temporal rate (dashed red curves) with the neural responses (black curves) at each individual site. This illustrates the ability of the modulation model to account for a rapid decrease in the spectrogram envelope without a corresponding decrease in the neural response.

The effect of sensitivity to fast modulation rates can also be observed when the modulation reconstruction is viewed in the spectrogram domain (FIG. 9, Panel B, middle, see Materials and Methods, Reconstruction Accuracy). The result is that dynamic spectral information (such as the upward frequency sweep at ~400-500 ms, FIG. 9, Panel B, top) is better resolved compared to the linear spectrogram-based reconstruction (FIG. 9, Panel B, bottom).

While these results indicate that a nonlinear model is required to reliably reconstruct fast modulation rates, psychoacoustic studies have shown that slow and intermediate modulation rates (~1-8 Hz) are most critical for speech intelligibility. These slow temporal fluctuations carry essential phonological information such as formant transitions and syllable rate. The linear spectrogram model, which also yielded good performance within this range (FIG. 7, Panel A; FIG. 13), therefore appears sufficient to reconstruct the essential range of temporal modulations. To examine this issue, reconstruction quality was further assessed by evaluating the ability to identify isolated words using the linear spectrogram reconstructions. A participant implanted with a high-density electrode grid (4 mm spacing) was analyzed, the density of which provided a large set of pSTG electrodes. Compared to lower density grid cases, data for this participant included ensemble frequency tuning that covered the majority of the (speech-related) acoustic spectrum (180-7, 000 Hz), a factor which was found to be important for accurate reconstruction (FIG. 6, Panel D). Spectrogram reconstructions were generated for each of 47 words, using neural responses either from single trials or averaged over 3-5 trials per word (same word set and cross-validated fitting procedure as described in FIG. 4, Panels A-C). To identify individual words from the reconstructions, a simple speech recognition algorithm based on dynamic time warping was used to temporally align words of variable duration. For a target word, a similarity score (correlation coefficient) was then computed between the target reconstruction and the actual spectrograms of each of the 47 words in the candidate set. The 47 similarity scores were sorted and word identification rank was quantified as the percentile rank of the correct word. (1.0 indicates the target reconstruction matched the correct word out of all candidate words; 0.0 indicates the target was least similar to the correct word among all other candidates.) The expected mean of the distribution of identification ranks is 0.5 at chance level.

Figure 10:
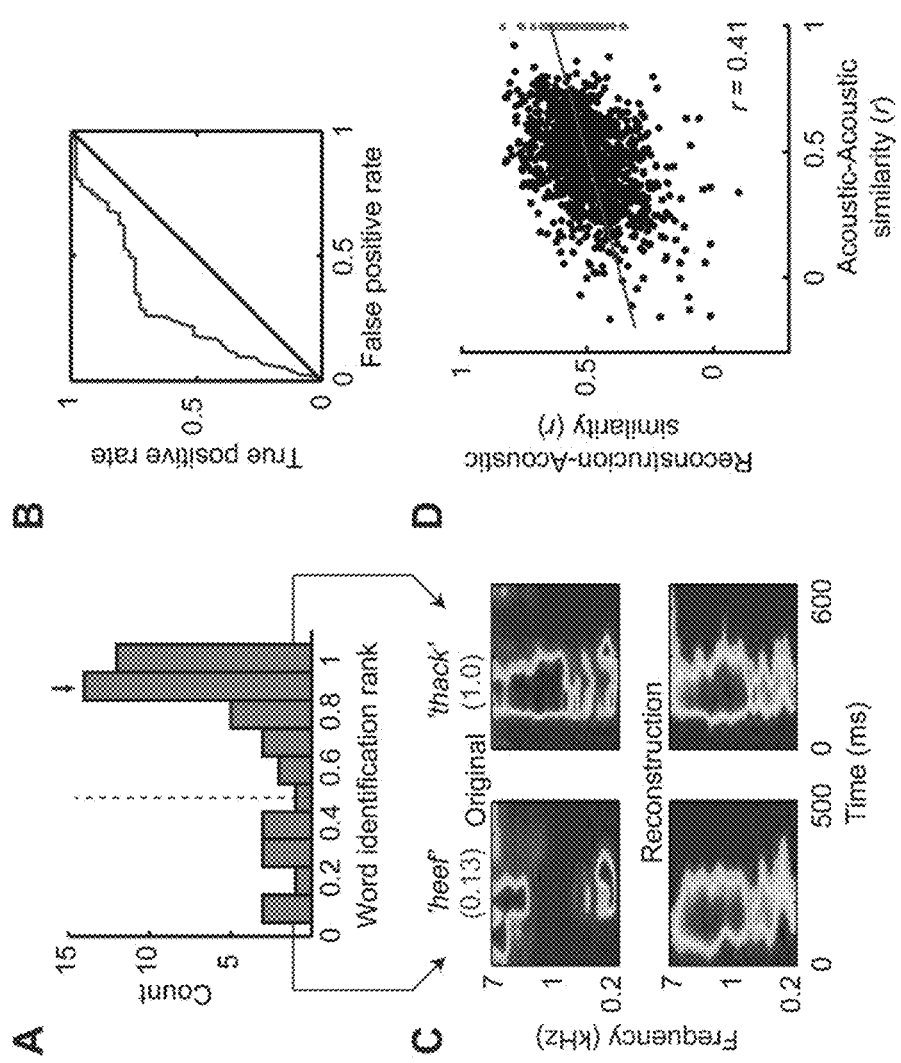
FIG. 10, Panels A-D depict word identification. Word identification based on the reconstructed spectrograms was assessed using a set of 47 individual words and pseudowords from a single speaker in a high density 4 mm grid experiment. The speech recognition algorithm is described in the text. Panel A: Distribution of identification rank for all 47 words in the set. Median identification rank is 0.89 (black arrow), which is higher than 0.50 chance level (dashed line; $p<0.0001$; randomization test). Statistical significance was assessed by a randomization test in which a null distribution of the median was constructed by randomly shuffling the word pairs 10,000 times, computing median identification rank for each shuffle, and calculating the percentile rank of the true median in the null distribution. Best performance was achieved after smoothing the spectrograms with a 2-D box filter (500 ms, 2 octaves). Panel B: Receiver operating characteristic (ROC) plot of identification performance (red curve). Diagonal black line indicates no predictive power. Panel C: Examples of accurately (right) and inaccurately (left) identified words. Left: reconstruction of pseudoword "heef" is poor and leads to a low identification rank (0.13). Right: reconstruction of pseudoword "thack" is accurate and best matches the correct word out of 46 other candidate words (identification rank=1.0). Panel D: Actual and reconstructed word similarity is correlated (r=0.41). Pair-wise similarity between the original spectrograms of individual words is correlated with pair-wise similarity between the reconstructed and original spectrograms. Plotted values are computed prior to spectrogram smoothing used in the identification algorithm. Gray points denote the similarity between identical words.
Figure 15:
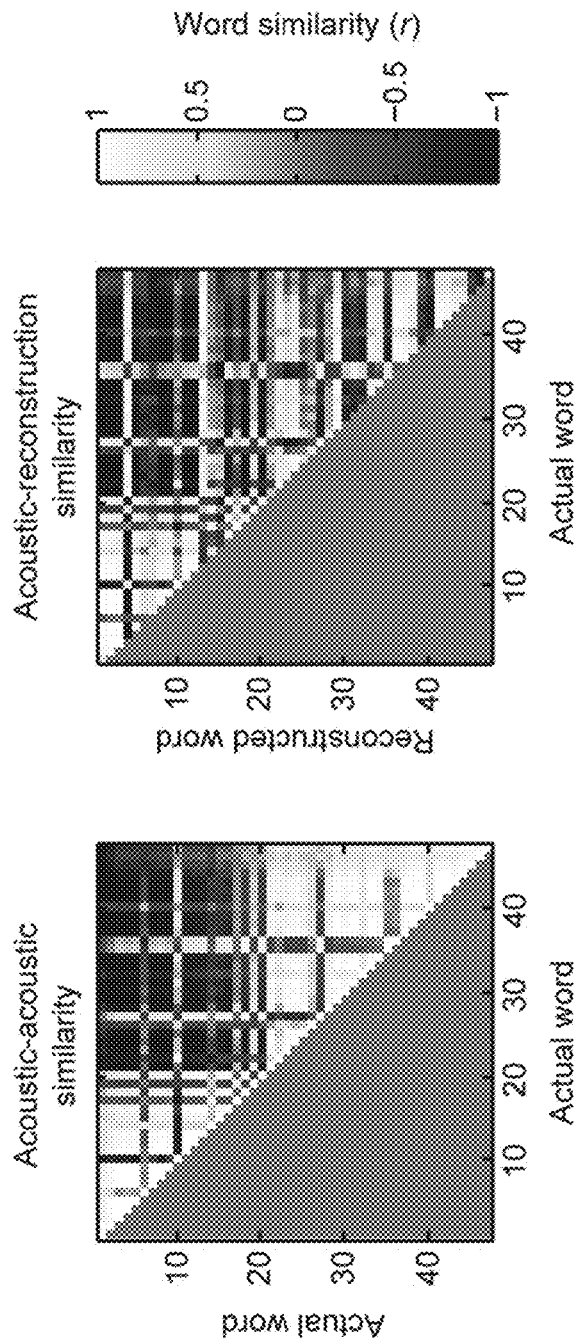
FIG. 15 shows confusion matrix for word identification (FIG. 10, Panels A-D). Left: pair-wise similarities (correlation coefficient) between actual auditory spectrograms of each word pair. Right: pair-wise similarities between reconstructed and actual spectrograms of each word pair. Correlations were computed prior to any spectrogram smoothing.

Word identification using averaged trials was substantially higher than chance (FIG. 10, Panels A-B, median identification rank=0.89, $p<0.0001$; randomization test), with correctly identified words exhibiting accurate reconstructions and poorly identified words exhibiting inaccurate reconstructions (FIG. 10, Panel C). For single trials, identification performance declined slightly but remained significant (median=0.76, $p<0.0001$; randomization test). In addition, for each possible word pair, the similarity between the two original spectrograms was computed and compared to the similarity between the reconstructed and actual spectrograms (using averaged trials; FIG. 10, Panel D; FIG. 15). Acoustic and reconstruction word similarities were correlated ($r=0.41$, $p<10^{-10}$, $df=45$), suggesting that acoustic similarity of the candidate words is likely to influence identification performance (i.e., identification is more difficult when the word set contains many acoustically similar sounds).

Example 2: Reconstruction of Imagined Speech from Brain Activity

Figure 18:
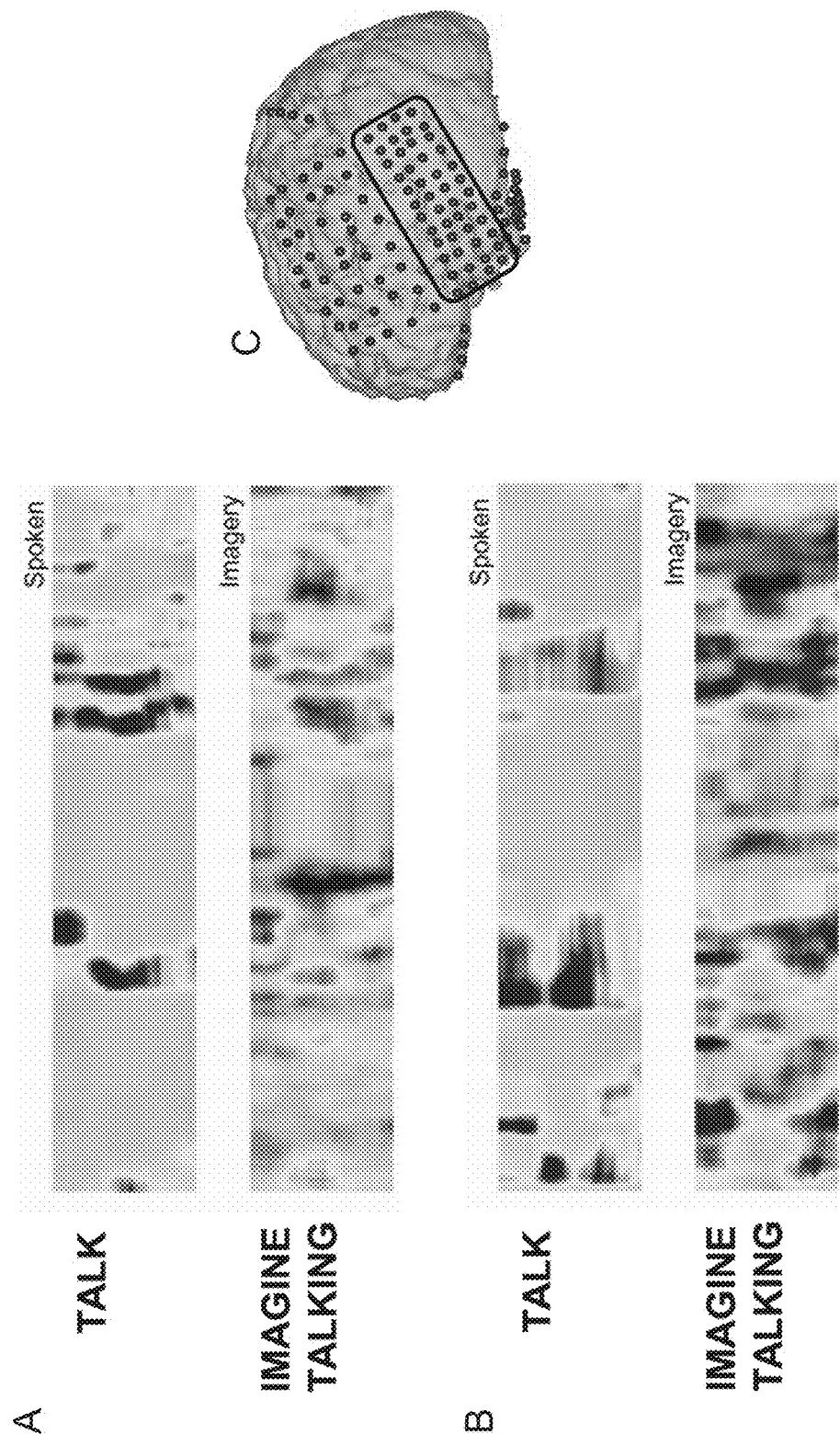
FIG. 18, Panels A-C show reconstructed spectrograms from heard and imagined speech. Subjects were given a ticker tape on which was written the Gettysburg Address. Each subject read the ticker tape aloud in its entirety, and the spectrogram was reconstructed. The top images of Panels A and B show two time points of the heard speech. The subject subsequently read the tickertape and was asked to imagine speaking the words. The bottom images of panels Panels A and B show two time points of such imagined speech. Panel C shows the placement of electrodes, with the black line indicating 48 electrodes of particular importance.

The text of the Gettysburg Address was printed on a ticker tape. The ticker tape was presented to 8 patients undergoing neurosurgical procedures for epilepsy or brain tumor. Cortical surface field potentials were recorded from non-penetrating multi-electrode arrays placed over the lateral temporal cortex, as described above in Materials and Methods, and in Example 1. The positioning of the electrodes is depicted in FIG. 18, Panel C.

Each patient was first asked to read the text of the Gettysburg Address aloud. Spectrograms were reconstructed using the algorithms and models described above. FIG. 18, Panels A-B show two time points of such spectrograms for one patient (labeled "Talk").

Each patient was subsequently asked to read the text of the Gettysburg Address while imagining that he or she was talking. The patient did not read the text aloud, nor was the text otherwise presented aurally to the patient. Spectrograms were reconstructed from the imagined speech brain activity, using algorithms and models described above. FIG. 18, Panels A-B show two time points of such spectrograms for one patient (labeled "Imagine Talking"). For 7 of the 8 patients, the word identification from imagined speech brain activity was substantially higher than chance.

Figure 19A:
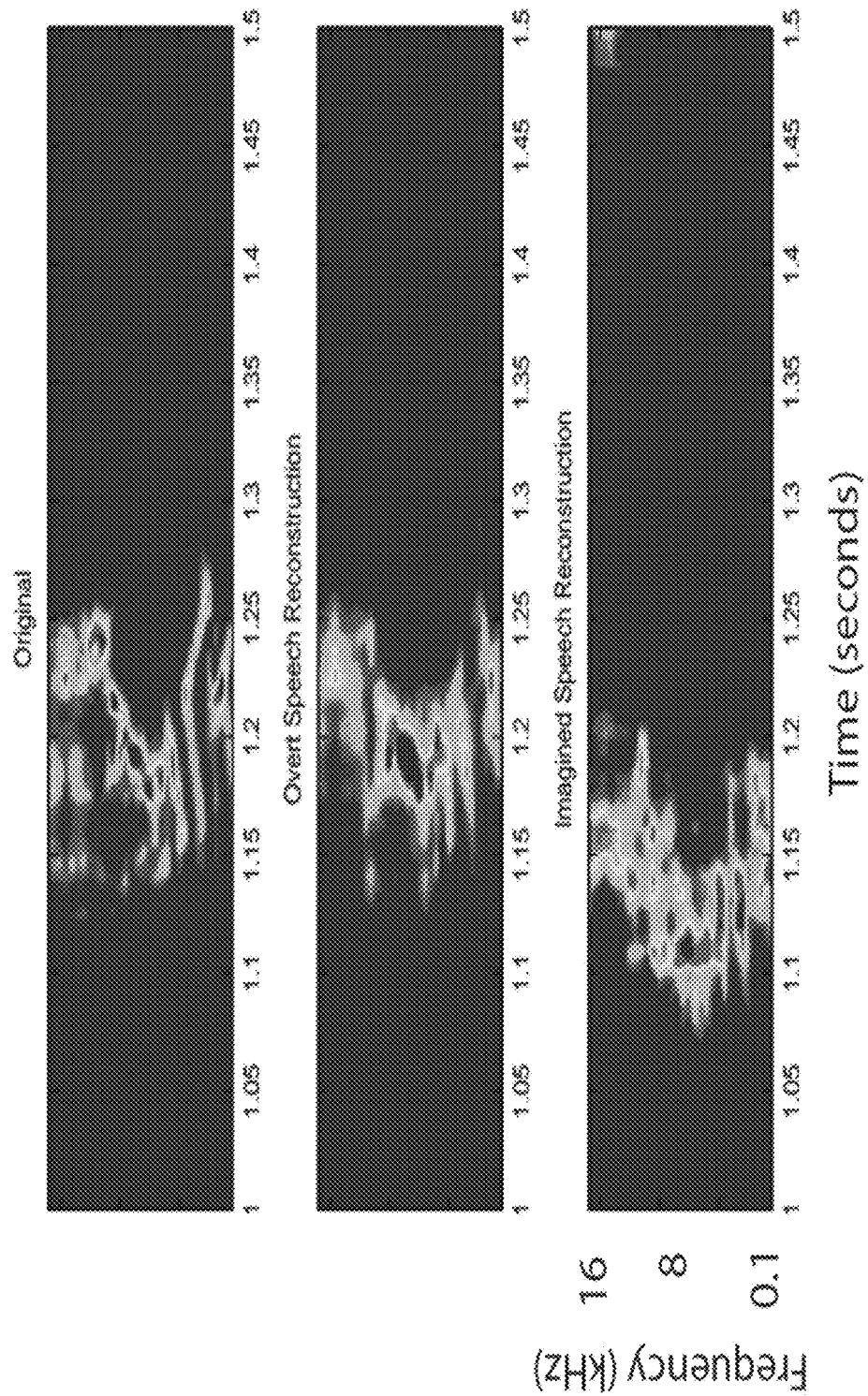
FIG. 19A, Panels A-C show an example decoding of speech imagery (silent speech) from measured brain activity. Top panel (A), Original Spectrogram of the sound of the sentence "How are you?". Middle panel (B), Predicted Spectrogram from brain activity while the patient spoke outloud the sentence "How are you?". Bottom panel (C), Predicted Spectrogram from brain activity while the patient silently imagined the sentence "How are you?". The predicted spectrotemporal pattern during silent imagery closely matches the spectrotemporal pattern of the actual sound, providing a basis to decode imagined speech.

FIG. 19A, Panels A-C. Example decoding of speech imagery (silent speech) from measured brain activity. Top panel (A), Original Spectrogram of the sound of the sentence "How are you?". Middle panel (B), Predicted Spectrogram from brain activity while the patient spoke outloud the sentence "How are you?". Bottom panel (C), Predicted Spectrogram from brain activity while the patient silently imagined the sentence "How are you?". The predicted spectrotemporal pattern during silent imagery closely matches the spectrotemporal pattern of the actual sound, providing a basis to decode imagined speech.

Figure 19B:
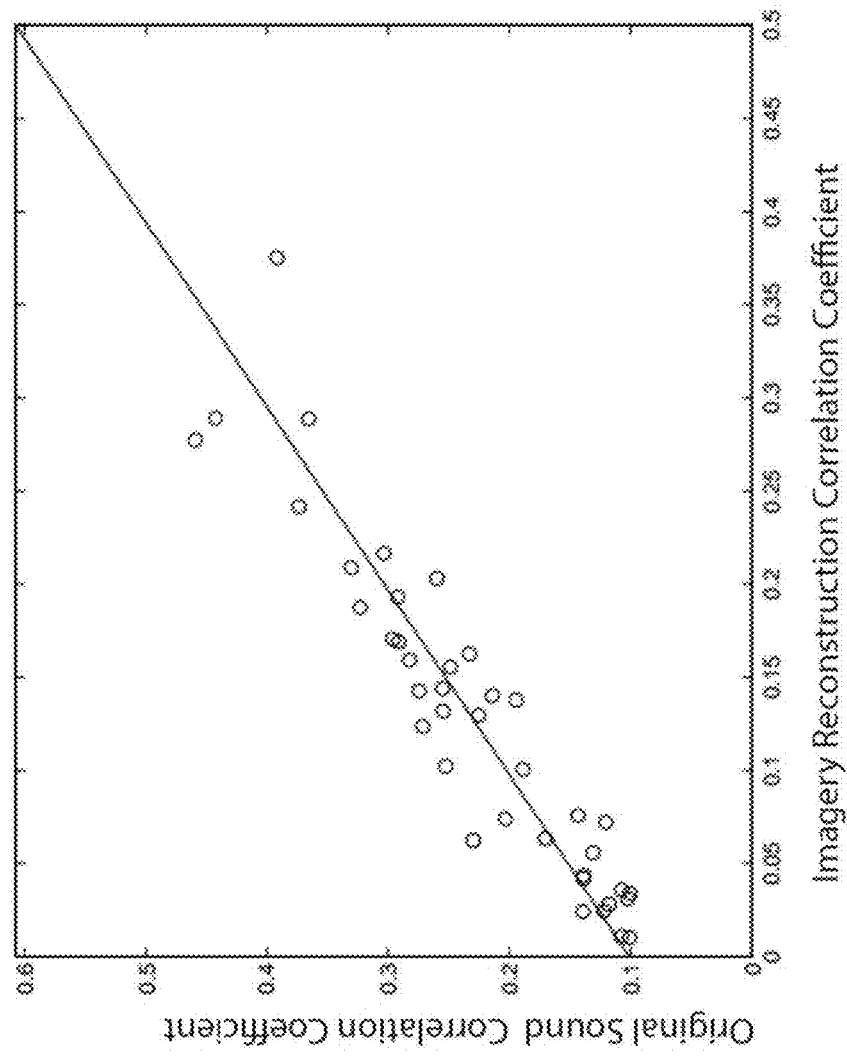
FIG. 19B shows individual electrodes (circles) having similar prediction accuracy for heard speech and imagined speech. For each individual electrode, a different reconstruction model is fit, and reconstruction accuracy (correlation coefficient) is assessed based on each electrode's model. This yields a correlation coefficient for each individual electrode that quantifies how well the brain activity at that electrode can be used to predict speech features. The figure shows that electrodes with high predictive power in the heard speech condition also have high predictive power in the imagery speech condition. Therefore, predictive models derived from heard speech can be successfully applied to decode imagined speech.

FIG. 19B. Individual electrodes (circles) have similar prediction accuracy for heard speech and imagined speech. For each individual electrode, a different reconstruction model is fit, and reconstruction accuracy (correlation coefficient) is assessed based on each electrode's model. This yields a correlation coefficient for each individual electrode that quantifies how well the brain activity at that electrode can be used to predict speech features. The figure shows that electrodes with high predictive power in the heard speech condition also have high predictive power in the imagery speech condition. Therefore, predictive models derived from heard speech can be successfully applied to decode imagined speech.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of decoding brain speech activity of a subject into speech feature data, the method comprising:
   (a) receiving brain speech activity data from two or more of; the anterior superior temporal gyrus (STG), medial superior temporal gyrus and posterior superior temporal gyrus of a subject into a decoder device;
   (b) processing the received brain speech activity data with a decoder module present in the decoder device, wherein the decoder module is configured to convert the received brain speech activity data by predictive statistical modeling into speech feature data; and
   (c) outputting the speech feature data to an output device, wherein the speech feature data is a representation of speech selected from the group consisting of auditory spectrograms, modulation representations, phonemes, phones, semantics, articulatory representations, nonlinear auditory representations, and motor representations of speech processing.

2. The method according to claim 1, wherein the brain speech activity data is obtained from an electrode device.

3. The method according to claim 2, wherein the electrode device comprises a plurality of electrodes.

4. The method according to claim 3, wherein the electrode device is implanted.

5. The method according to claim 4, wherein the brain speech activity data is electrocorticography (ECoG) data.

6. The method according to claim 3, wherein the electrode device is not implanted.

7. The method according to claim 6, wherein the brain speech activity data is electroencephalography (EEG) data.

8. The method according to claim 1, wherein the decoder module employs at least one of a linear spectrogram model and a non-linear modulation model.

9. The method according to claim 8, wherein the decoder module is configured to select between a linear spectrogram model and a non-linear modulation model.

10. The method according to claim 1, wherein the speech feature data is configured to be converted by an output device into readable text.

11. The method according to claim 1, wherein the speech feature data is configured to be converted by an output device into audible sound.

12. The method according to claim 11, wherein the audible sound is a human recognizable word.

13. The method according to claim 11, wherein the audible sound is a human recognizable collection of words.

14. The method according to claim 13, wherein the human recognizable collection comprises phrases or sentences.

15. The method according to claim 1, wherein the brain speech activity data is a result of heard speech.

16. The method according to claim 1, wherein the brain speech activity data is the result of imagined speech.

17. The method according to claim 1, wherein predictive statistical modeling comprises linear spectrogram modeling, non-linear modulation modeling or a combination thereof.

18. The method according to claim 17, wherein the non-linear modulation modeling comprises generating a modulation model by employing a plurality of modulation selective filters that analyze a two-dimensional spectrogram and extract modulation energy at different temporal rates and spectral scales.

19. The method according to claim 17, wherein linear spectrogram modeling further comprises mapping a stimulus spectrogram.

20. The method according to claim 19, wherein the stimulus spectrogram exhibits frequency selectivity.

21. The method according to claim 20, wherein frequency selectivity comprises neural response amplitudes based on stimulus frequency.

22. The method according to claim 1, wherein the method comprises receiving brain speech activity data from across the superior temporal gyms (STG) of the subject into the decoder device.

23. The method according to claim 1, further comprising receiving brain speech activity data from the middle temporal gyrus.

24. A system for decoding brain speech activity of a subject into speech feature data, the system comprising:
   a decoder device comprising:
      a data input component configured to receive brain speech activity data from two or more of: the anterior superior temporal gyrus (STG)), medial superior temporal gyrus and posterior superior temporal gyrus of a subject;
      a decoder module comprising:
         a processor; and
         a machine-readable medium encoding instructions operable to:
            cause the processor to convert received brain speech activity data by predictive statistical modeling into speech feature data; and
            output the speech feature data to an output component; and
      a data output component configured to output speech feature data from the decoder module,
      wherein the speech feature data is a representation of speech selected from the group consisting of auditory spectrograms, modulation representations, phonemes, phones, semantics, articulatory representations, nonlinear auditory representations, and motor representations of speech processing.

25. The system according to claim 24, wherein the data input component is configured to receive brain speech activity data from across the superior temporal gyrus (STG) of the subject into the decoder device.

26. The system according to claim 24, wherein the data input component is further configured to receive brain speech activity data from the middle temporal gyrus.

* * * * *